(12) United States Patent
Plahey et al.

(10) Patent No.: US 11,654,220 B2
(45) Date of Patent: May 23, 2023

(54) PATIENT LINE CHECK AND OCCLUSION DETECTION FOR A DIALYSIS MACHINE USING ADJUSTED PUMP OPERATING PARAMETERS

(71) Applicant: Fresenius Medical Care Holdings, Inc., Waltham, MA (US)

(72) Inventors: Kulwinder S. Plahey, Martinez, CA (US); Jie Zhu, Brentwood, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 622 days.

(21) Appl. No.: 16/447,759

(22) Filed: Jun. 20, 2019

(65) Prior Publication Data

US 2020/0397969 A1 Dec. 24, 2020

(51) Int. Cl.
*A61M 1/28* (2006.01)
*A61M 39/08* (2006.01)

(52) U.S. Cl.
CPC ............ *A61M 1/281* (2014.02); *A61M 39/08* (2013.01); *A61M 2205/106* (2013.01); *A61M 2205/12* (2013.01); *A61M 2205/18* (2013.01); *A61M 2205/3334* (2013.01); *A61M 2205/3386* (2013.01); *A61M 2205/50* (2013.01)

(58) Field of Classification Search
CPC ........ A61M 1/28; A61M 1/281; A61M 1/282; A61M 5/14224; A61M 2005/14208; A61M 2205/106; A61M 2205/12; A61M 2205/121; A61M 2205/122; A61M 2205/128; A61M 2205/18; A61M 2205/3334; A61M 2205/3386
See application file for complete search history.

(56) References Cited

U.S. PATENT DOCUMENTS

| | | | |
|---|---|---|---|
| 7,575,564 B2 | 8/2009 | Childers | |
| 8,070,709 B2 | 12/2011 | Childers | |
| 8,684,971 B2 | 4/2014 | Busby et al. | |
| 8,900,174 B2 | 12/2014 | Childers | |
| 9,861,733 B2 | 1/2018 | Burbank et al. | |
| 10,172,993 B2 | 1/2019 | Crawford et al. | |
| 10,201,647 B2 | 2/2019 | Norris et al. | |
| 2009/0012461 A1 | 1/2009 | Childers et al. | |
| 2011/0160649 A1 | 6/2011 | Pan | |
| 2013/0106609 A1 | 5/2013 | Singh et al. | |
| 2018/0001009 A1 | 1/2018 | Crawford et al. | |

OTHER PUBLICATIONS

International Patent Application No. PCT/US2020/037319—Search Report (Sep. 3, 2020).

*Primary Examiner* — Kami A Bosworth
(74) *Attorney, Agent, or Firm* — Leydig, Voit & Mayer, Ltd.

(57) ABSTRACT

A dialysis machine (e.g., a peritoneal dialysis (PD) machine) can include a patient line that provides dialysate solution to a patient and removes effluent dialysate from the patient through a catheter. During a drain phase of a PD treatment, an occlusion can occur at different locations in the patient line and/or catheter. A pressure sensor can detect a change in pressure of the fluid at the proximal end of the patient line to infer a potential occlusion in the patient line. Prior to setting an alarm to alert the patient of the blockage in the patient line, operating parameters of the PD machine can be changed to attempt to correct the issue. In an embodiment, the pump mechanism can be cycled at a reduced speed or a reduced rate in order to confirm the occlusion or attempt to alleviate the low fluid flow condition before the alarm is set.

17 Claims, 26 Drawing Sheets

PATIENT LINE CHECK AND OCCLUSION DETECTION FOR A DIALYSIS MACHINE USING ADJUSTED PUMP OPERATING PARAMETERS

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option pumps dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum function as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles.

Automated PD machines, sometimes referred to as PD cyclers, are designed to control the PD treatment process so that it can be performed at home without clinical staff, typically while the patient sleeps overnight. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

The PD cyclers currently on the market enable the patient to complete dialysis treatment at night rather than in a clinical setting during the day like hemodialysis treatment, which minimizes the interference with the patient's life. However, even though the PD cyclers automate much of the process of the PD treatment, the machines cannot control every aspect of the treatment. For example, patients can roll over in their sleep and obstruct the patient line that is used to fill and drain the dialysis from the patient's peritoneal cavity. If the patient line is occluded or obstructed, then the PD machine alerts the patient to request corrective action to clear the occlusion. Most patients would prefer to be minimally involved in the PD treatment process while they sleep. PD cyclers can be designed to attempt to correct some of the issues they discover, but conventional methods for inferring the state of the patient line are not ideal.

SUMMARY

A PD system is provided for performing a PD treatment. The PD system can include at least one pump, a cassette, and a processor. The at least one pump is configured to provide fluid to or withdraw fluid from a line connected to a catheter inserted into a peritoneal cavity of a patient. The cassette includes at least one pump chamber and at least one pressure sensing chamber fluidly coupled to the at least one pump chamber. The line is fluidly coupled to the at least one pump chamber in the cassette.

In an embodiment, the processor can be configured to detect a low fluid flow condition during a phase of a PD cycle. In response to the low fluid flow condition, the processor is configured to adjust operating parameters of the at least one pump to reduce a speed of the at least one pump from a first speed to a second speed that is less than the first speed. After the operating parameters are adjusted, the processor is further configured to detect a low fluid volume condition while the at least one pump is operated at the second speed. In response to the low fluid volume condition, the processor can be configured to trigger an alarm and/or terminate the phase of the PD cycle.

In an embodiment, a method of operating a PD machine includes steps for operating one or more pumps during a drain phase of a PD cycle to drain effluent dialysate from a peritoneal cavity of a patient fluidly coupled to the PD machine, detecting a low fluid flow condition during the drain phase, adjusting, responsive to the low fluid flow condition, operating parameters of the one or more pumps to reduce an expected flow rate through the patient line, detecting, after adjusting the operating parameters to reduce the expected flow rate, a low fluid volume condition, and terminating the drain phase of the PD cycle. A distal end of a patient line is attached to a catheter inserted into the peritoneal cavity of the patient and a proximal end of the patient line is attached to a port of the PD machine.

In an embodiment, a medical device is provided for performing a PD treatment. The medical device includes a distensible medical tube having a proximal end connected to a port of the medical device and one or more pumps configured to direct a flow of fluid in the distensible medical tube. The medical device further includes a pressure sensor disposed at the proximal end of the distensible medical tube. The pressure sensor can be configured to measure a fluid pressure in a pressure sensing chamber fluidly coupled to the distensible medical tube. The medical device further includes a control unit configured to detect a low flow condition and perform a line check procedure to determine whether the distensible medical tube includes an occlusion. The line check procedure includes steps for adjusting operating parameters of the one or more pumps while maintaining a direction of fluid flow in the distensible medical tube and monitoring a pressure sensor signal to detect a low fluid volume condition.

DETAILED DESCRIPTION

A peritoneal dialysis (PD) machine can be designed to perform corrective action in response to a low fluid flow condition prior to alerting the patient of a potential issue during treatment. In conventional PD cyclers, a low fluid flow condition can be detected at the proximal end of the patient line. For example, a pressure sensor or other sensing means can be used to detect that the flow rate of fluid from the patient line entering the PD machine is lower than a threshold value. In response to the low fluid flow condition, the PD machine can set an alarm and stop treatment temporarily until the patient or a caregiver clears the alarm. Prior to setting the alarm, some conventional PD machines can attempt to clear a possible occlusion by reversing the flow of fluid in the patient line to push a small amount of fluid back into the patient's peritoneal cavity. A fluid pressure can be monitored while the fluid flow is reversed to determine if the patient line is clear or if there is a likely occlusion in the patient line. Treatment can then continue or be temporarily halted based on the outcome of the patient line check procedure. However, the conventional patient line check procedure is detrimental because it involves returning waste products to the patient's peritoneal cavity and increases the time required for the drain phase of the PD cycle.

In some embodiments, a patient line check procedure is provided in which the direction of fluid flow in the patient line is not reversed. Instead, in response to a low fluid flow condition being detected during normal operating conditions in the drain phase of the PD cycle, the operating parameters of the PD machine are adjusted to slow down the operating speed of the one or more pumps of the PD machine. The term "slow down" in this context can refer to, e.g., reducing an expected flow rate of the pump, reducing a linear speed of a piston included in the pump mechanism, or reducing a cycle frequency of the pump mechanism. By slowing down the speed of the pumping mechanism, the issue causing the low fluid flow condition may be alleviated. For example, a pressure differential between the proximal and distal ends of the patient line can be reduced, more fluid is allowed to flow through a partially restricted orifice, or the like. The PD machine can monitor fluid flow rates and or fluid volume in the pump chambers to determine if there is a likely occlusion in the patient line or if the low fluid flow condition is corrected by the new operating parameters. After the patient line check procedure is performed, the PD treatment can continue with the new operating parameters or the operating parameters can be reset to operate in the normal operating condition during the drain phase of the PD cycle.

Figure 1:
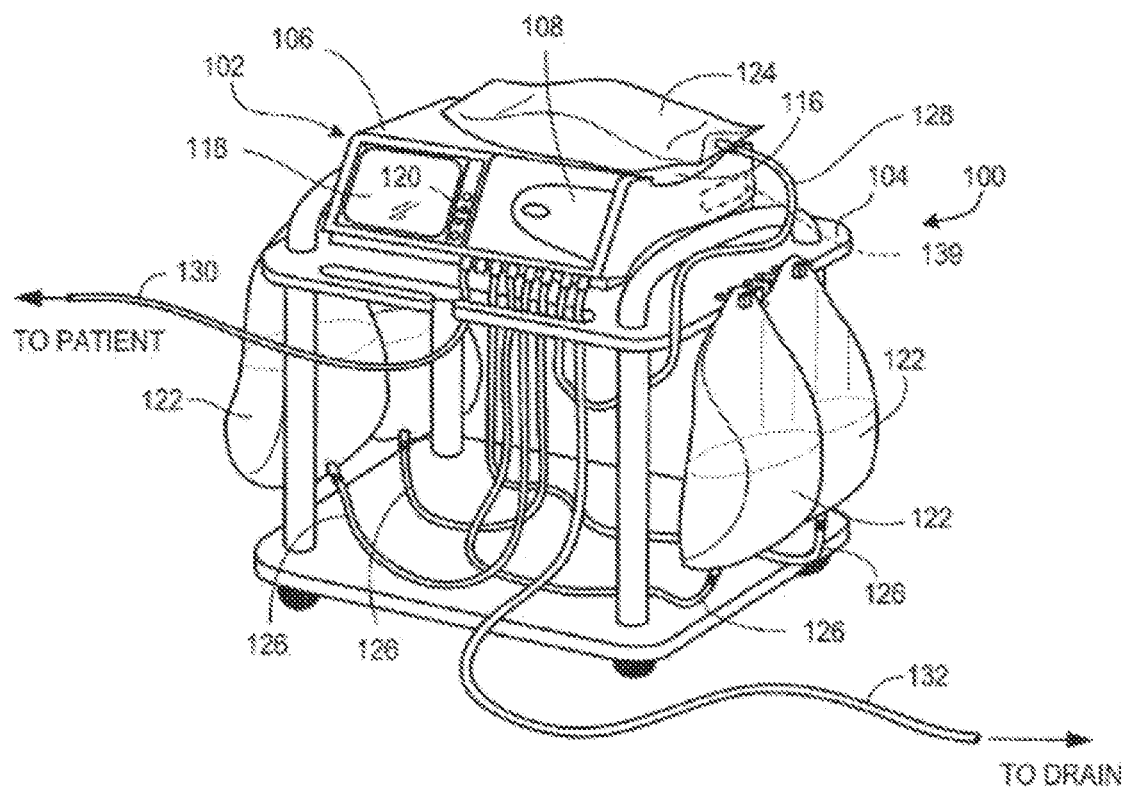
FIG. 1 illustrates a peritoneal dialysis (PD) system, in accordance with some embodiments.

FIG. 1 illustrates a peritoneal dialysis (PD) system 100, in accordance with some embodiments. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc.

Figure 2:
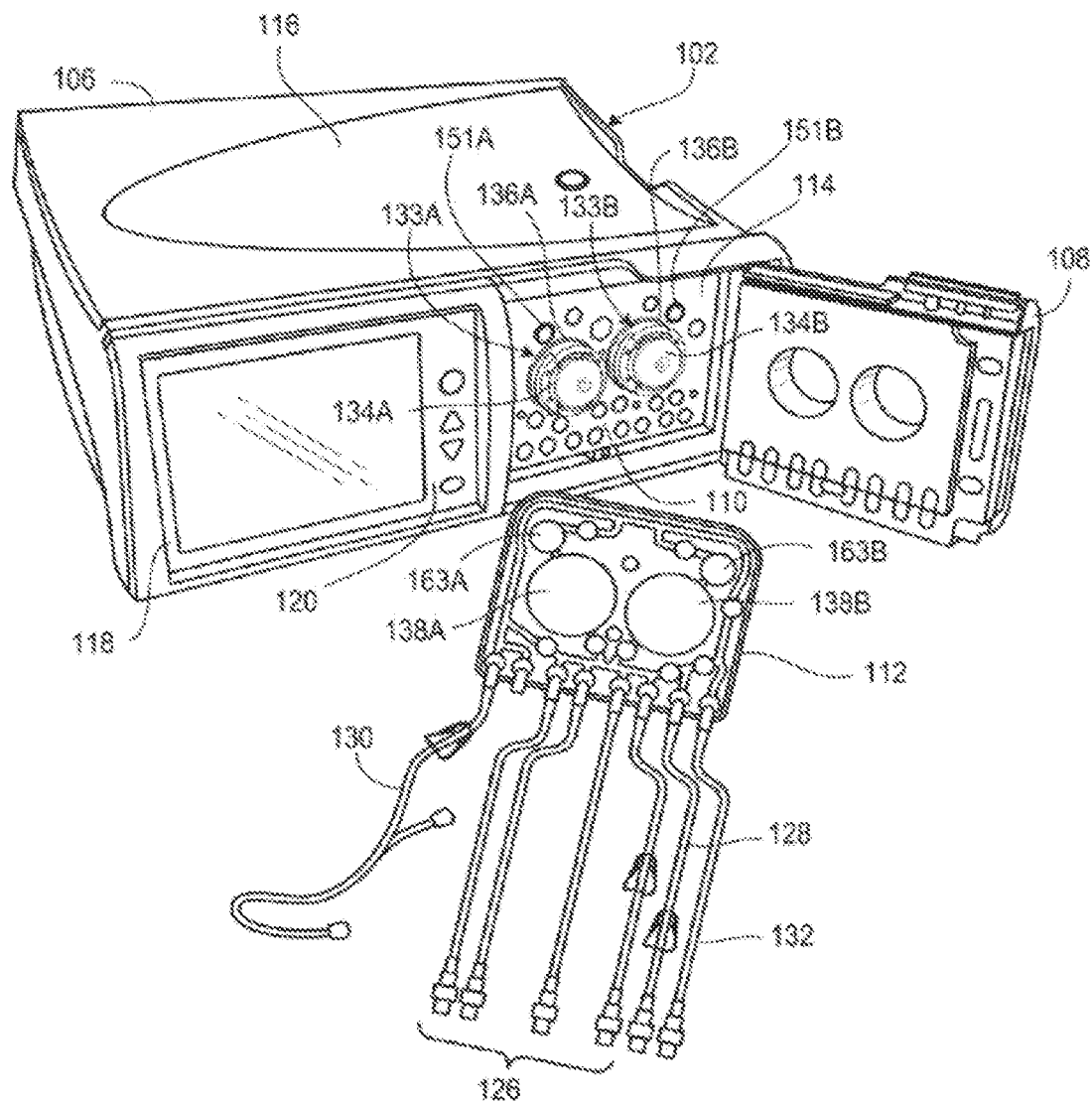
FIG. 2 is a perspective view of the PD machine and the PD cassette of the PD system of FIG. 1, in accordance with some embodiments

FIG. 2 is a perspective view of the PD machine 102 and the PD cassette 112 of the PD system 100 of FIG. 1, in accordance with some embodiments. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts (not explicitly shown). The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance vacuum around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
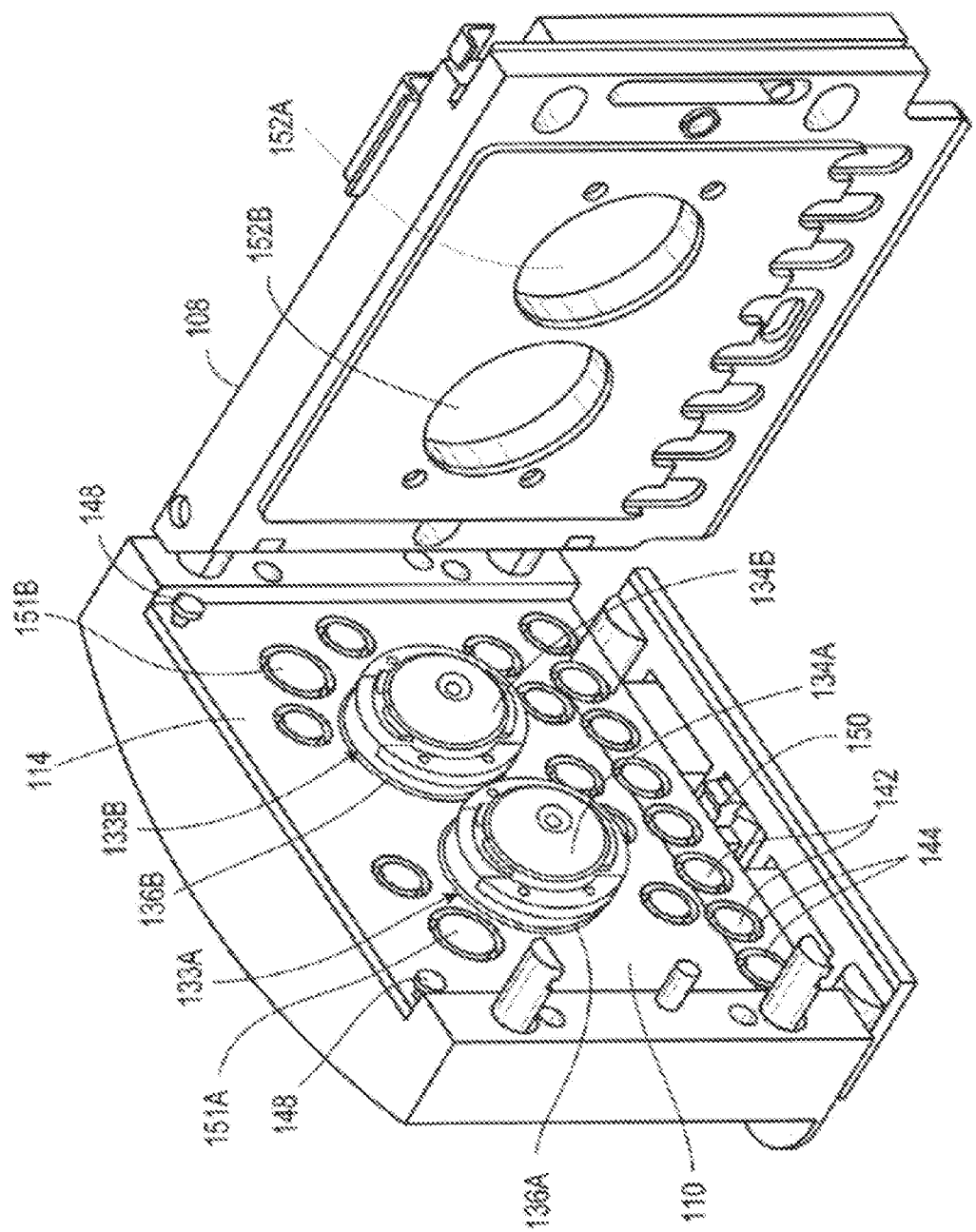
FIG. 3 is a perspective view of an open cassette compartment of the PD machine of FIG. 1, in accordance with some embodiments.

FIG. 3 is a perspective view of an open cassette compartment 114 of the PD machine 102 of FIG. 1, in accordance with some embodiments. As discussed above, the PD machine 102 includes pistons 133A, 133B disposed in piston access ports 136A, 136B, respectively. The PD machine 102 also includes multiple inflatable members 142 positioned within inflatable member ports 144 in the cassette interface 110. The inflatable members 142 align with depressible dome regions of the cassette 112 when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions of the cassette 112. The inflatable members 142 act, in cooperation with the depressible dome regions, as valves to direct dialysate through the cassette 112 in a desired manner during use. In particular, the inflatable members 142 bulge outward beyond the surface of the cassette interface 110 and into contact with the depressible dome regions of the cassette 112 when inflated, and retract into the inflatable member ports 144 and out of contact with the cassette 112 when deflated. By inflating certain inflatable members 142 to depress their associated dome regions on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

In some embodiments, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102 defines cylindrical recesses 152A, 152B that substantially align with the pistons 133A, 133B when the door 108 is in the closed position. When the cassette 112 is positioned within the cassette compartment 114 with the door 108 closed, the pump chambers 138A, 138B at least partially fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the surface of the pump chambers 138A, 138B, and the other portions of the door 108 support the other regions or surfaces of the cassette 112. The door 108 can counteract the forces applied by the inflatable members 142 and, therefore, allows the inflatable members 142 to actuate the depressible dome regions on the cassette 112. The engagement between the door 108 and the cassette 112 can also help to hold the cassette 112 in a desired position within the cassette compartment 114 to further ensure that the pistons 133A, 133B align with the fluid pump chambers 138A, 138B of the cassette 112.

The control unit 139 of FIG. 1 is connected to the pressure sensors 151A, 151B, to the stepper motors (e.g., the drivers for the stepper motors) that drive the pistons 133A, 133B, and to the encoders that monitor rotation of the lead screws attached to the stepper motors such that the control unit 139 can receive signals from and transmit signals to those components of the PD system 100. The control unit 139 monitors the components to which it is connected to determine whether any complications exist within the PD system 100, such as the presence of an occlusion or blockage in the patient line 130.

Figure 4:
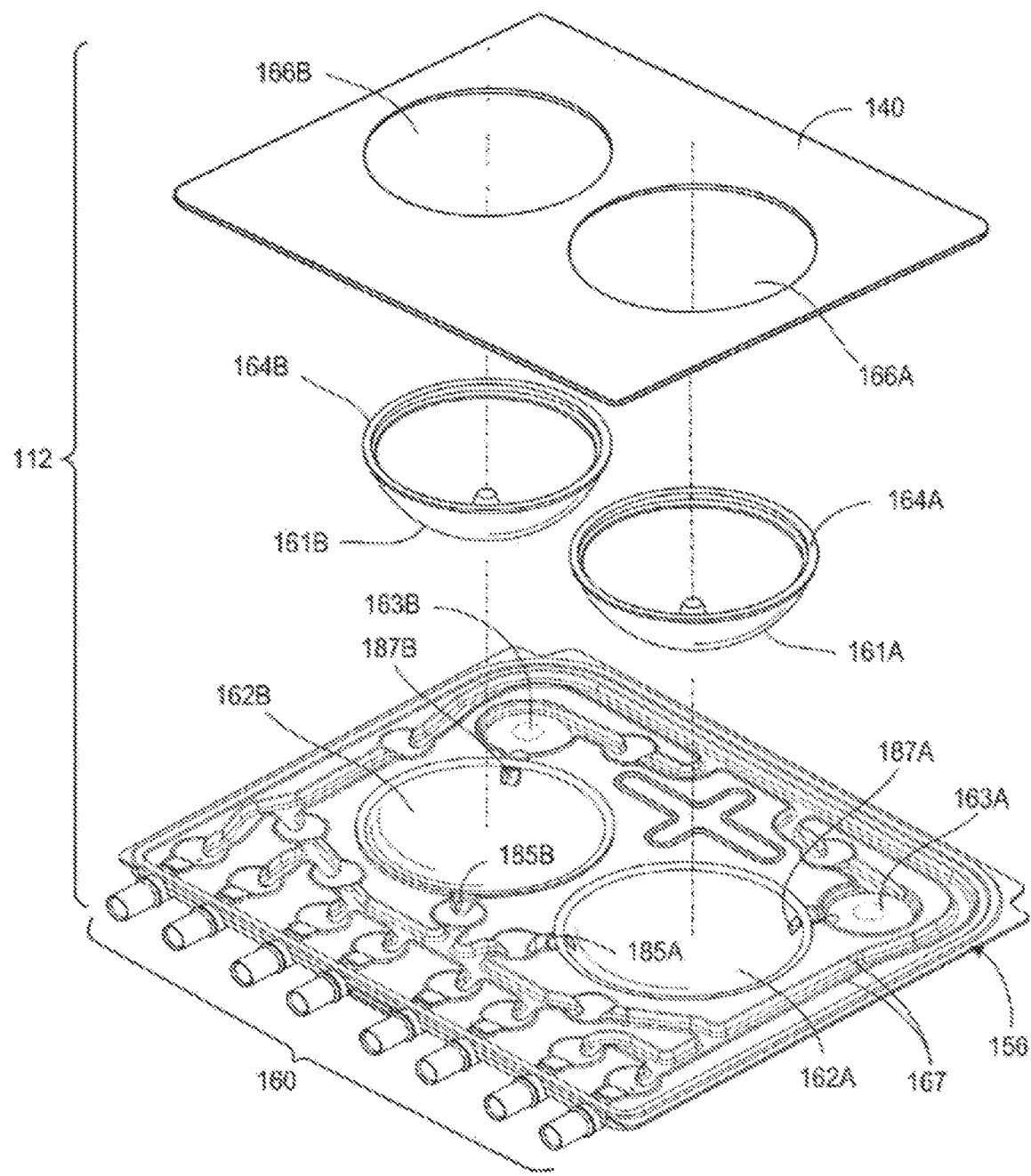
FIG. 4 is an exploded, perspective view of the PD cassette of FIG. 2, in accordance with some embodiments.
Figure 5:
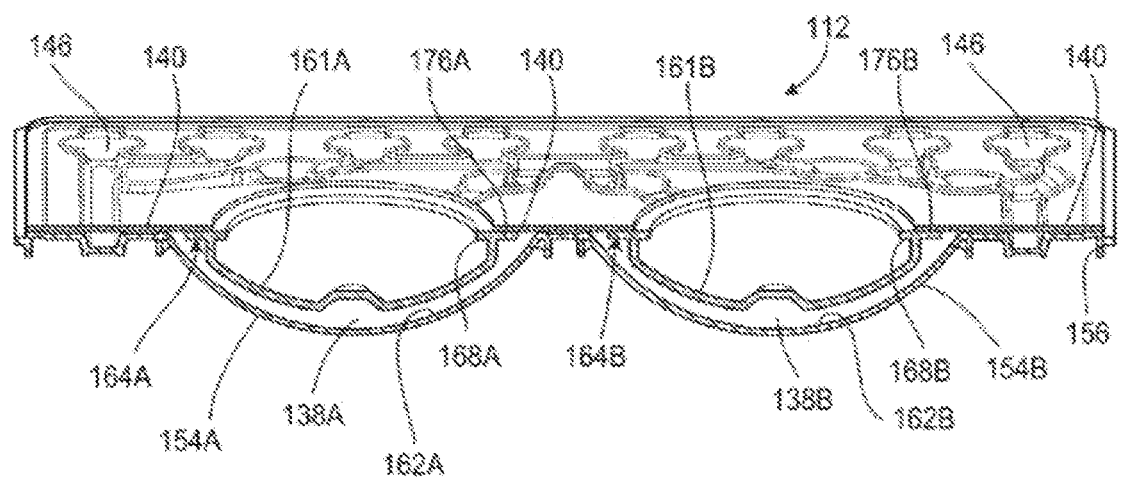
FIG. 5 is a cross-sectional view of the fully assembled PD cassette of FIG. 2, in accordance with some embodiments.
Figure 6:
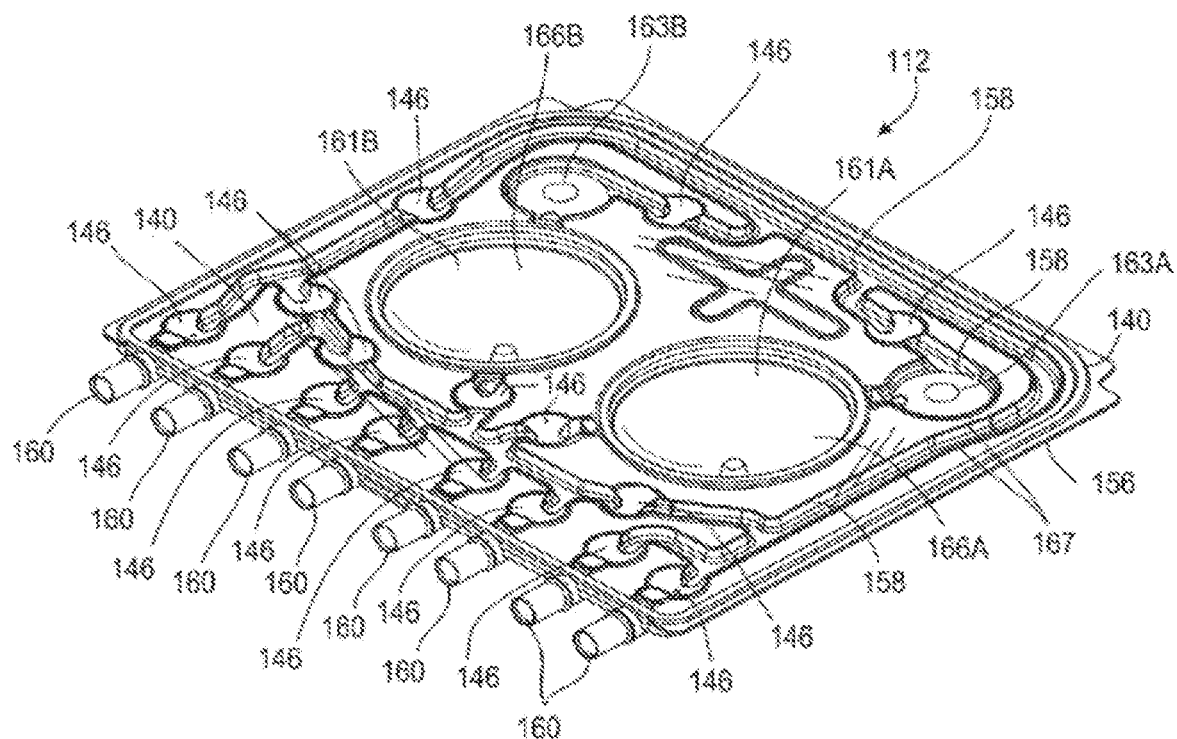
FIGS. 6 and 7 are perspective views of the PD cassette of FIG. 2 from a front side and a back side, respectively, in accordance with some embodiments.
Figure 7:
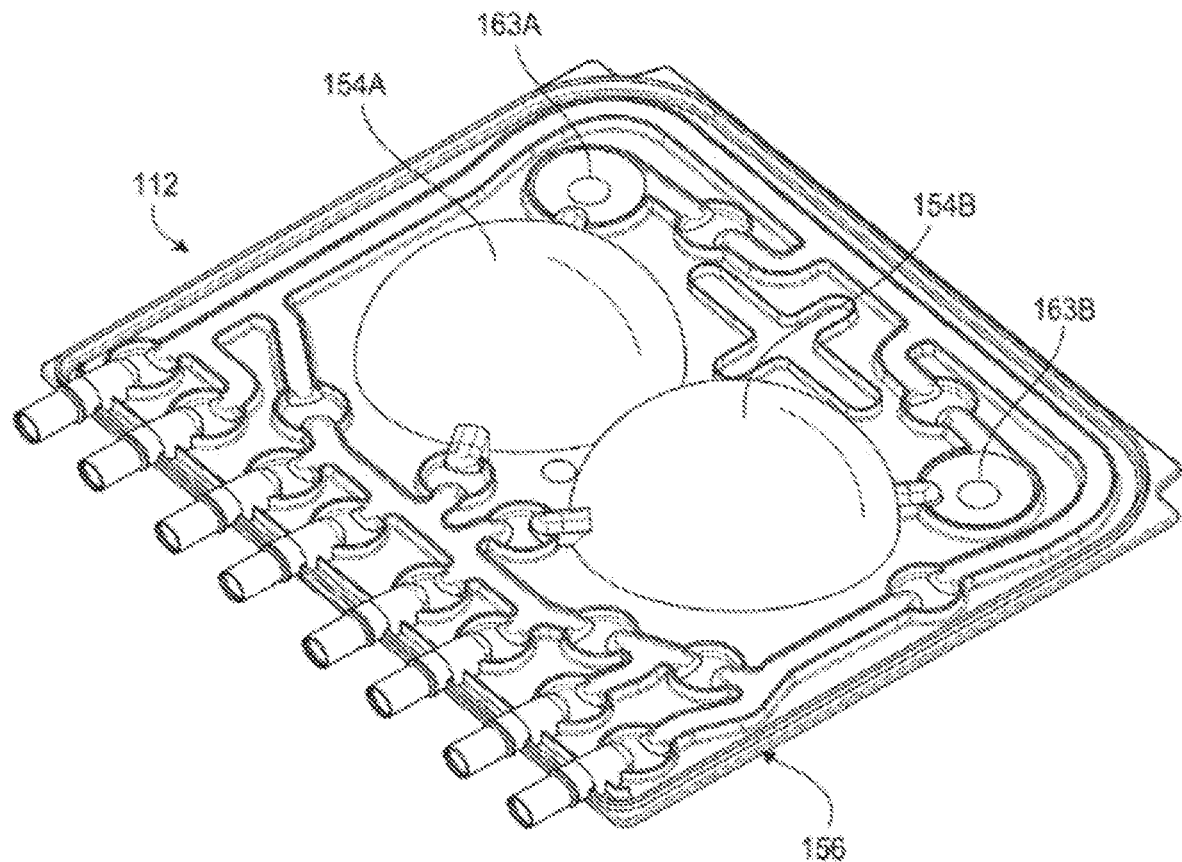

FIG. 4 is an exploded, perspective view of the PD cassette 112 of FIG. 2, in accordance with some embodiments. FIG. 5 is a cross-sectional view of the fully assembled PD cassette 112 of FIG. 2, in accordance with some embodiments. FIGS. 6 and 7 are perspective views of the PD cassette 112 of FIG. 2 from a front side and a back side, respectively, in accordance with some embodiments.

As depicted in FIGS. 4-7, the PD cassette 112 includes a flexible membrane 140 that is attached to a periphery of a tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some embodiments, the dome-shaped fastening members 161A, 161B have a diameter, measured from the outer edges of annular flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 1334B. Because the membrane 140 is attached to the dome-shaped fastening members 161A, 161B, movement of the dome-shaped fastening members 161A, 161B into and out of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable members 142 of the PD machine 102 act on the cassette 112 during use. The dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of the dialysate through the cassette 112 can be controlled through the selective depression of the depressible dome regions 146 by selectively inflating the inflatable members 142 of the PD machine 102.

The fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette 112, as depicted in FIGS. 1 & 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B or to allow fluid to flow from any of ports 185A, 185B, 187A, and 187B of the pump chambers 138A, 138B to any of the lines 126, 128, 130, and 132.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some embodiments, these components of the cassette 112 are formed of one or more polymers, such as polypropylene, polyvinyl chloride, polycarbonate, polysulfone, and other medical grade plastic materials. In some embodiments, these components can be formed of one or more metals or alloys, such as stainless steel. These components can alternatively be formed of various different combinations of the above-noted polymers and/or metals/alloys. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some embodiments, the membrane 140 is about 0.100 micron to about 0.150 micron in thickness. However, various other thicknesses may be sufficient depending on the type of material used to form the membrane 140. Any of various different materials that permit the membrane 140 to deflect in response to movement of the inflatable members 142 without tearing can be used to form the membrane 140. In some embodiments, the membrane 140 includes a three-layer laminate. In some embodiments, inner and outer layers of the laminate are formed of a compound that is made up of 60 percent Septon® 8004 thermoplastic rubber (i.e., hydrogenated styenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octane copolymer), and 35 percent Septon® 8004 thermoplastic rubber (i.e., hydrogenated styrenic block copolymer). The membrane 140 can alternatively include more or fewer layers and/or can be formed of different materials.

Figure 8:
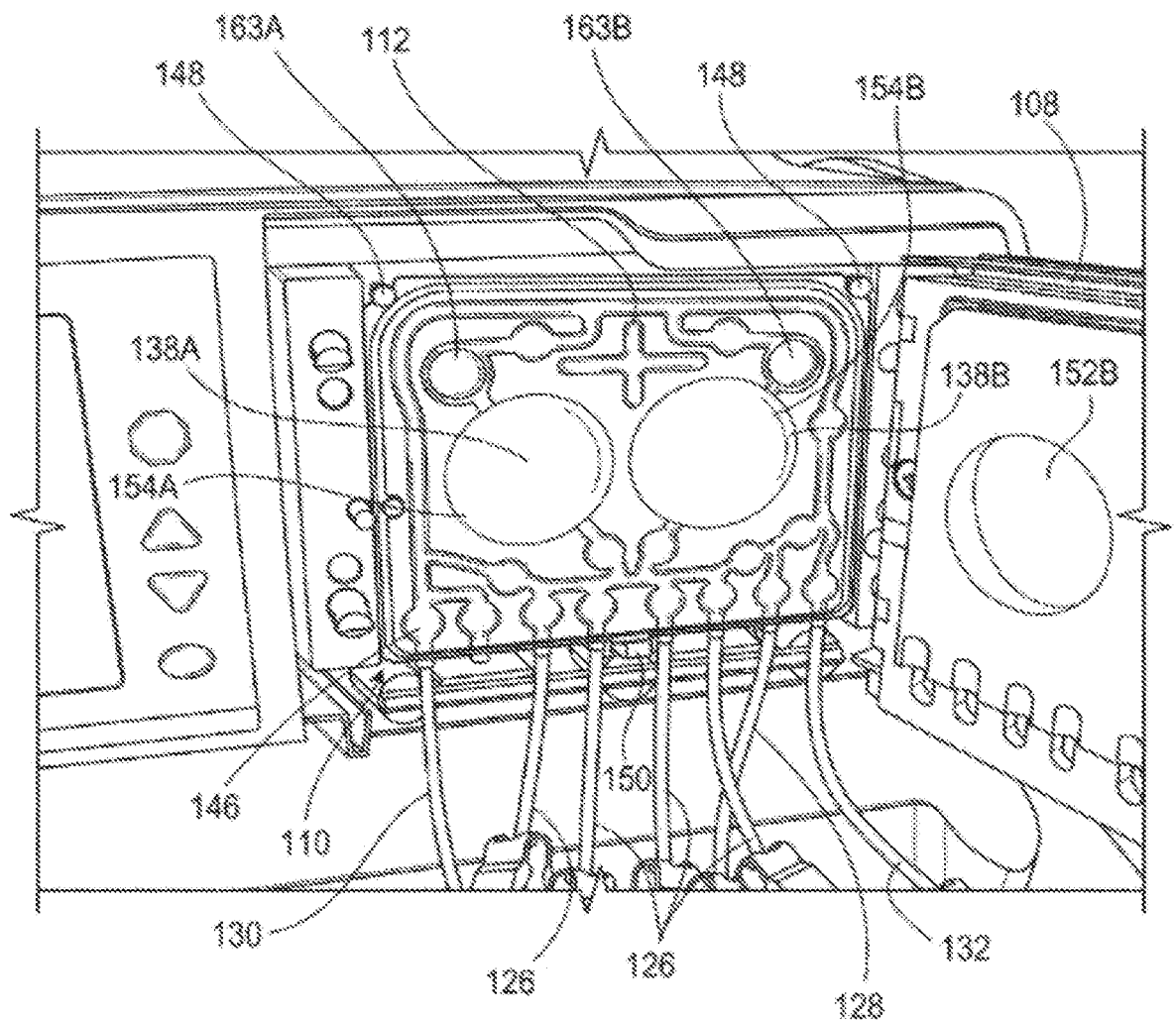
FIG. 8 illustrates the PD cassette seated against the cassette interface, in accordance with some embodiments.

FIG. 8 illustrates the PD cassette 112 seated against the cassette interface 110, in accordance with some embodiments. As depicted in FIG. 8, before starting a PD treatment, the door 108 of the PD machine 102 is opened to expose the cassette interface 110, and the cassette 112 is positioned with the dome-shaped fastening members 161A, 161B aligned with the pistons 133A, 133B of the PD machine 102, the pressure sensing chambers 163A, 163B aligned with the pressure sensors 151A, 151B of the PD machine 102, the depressible dome regions 146 aligned with the inflatable members 142 of the PD machine 102, and the membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette 112 act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward towards the door 108. The pistons 133A, 133B are typically retracted into the piston access ports 136A, 136B during installation of the cassette 112 to avoid interference between pistons 133A, 133B and the dome-shaped fastening members 161A, 161B and, therefore, increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. The compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146. The patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to the dome-shaped fastening members 161A, 161B of the cassette 112 to permit priming of the cassette 112 and one or more of the lines 126, 128, 130, and 132. Once these components have been primed, the PD treatment can be initiated.

FIGS. 9A-9G are cross-sectional views of the PD system 100 at various stages of setup, priming, and treatment, in accordance with some embodiments. The portion of the PD system 100 depicted in FIGS. 9A-9G focus on the interaction between the piston 133A of the PD machine 102 and the pump chamber 138A of the cassette 112 during the setup, priming, and treatment. The interaction between the other piston 133B and the other pump chamber 138B is similar to that shown in FIGS. 9A-9G and, therefore, will not be separately described herein to avoid repetition.

Figure 9A:
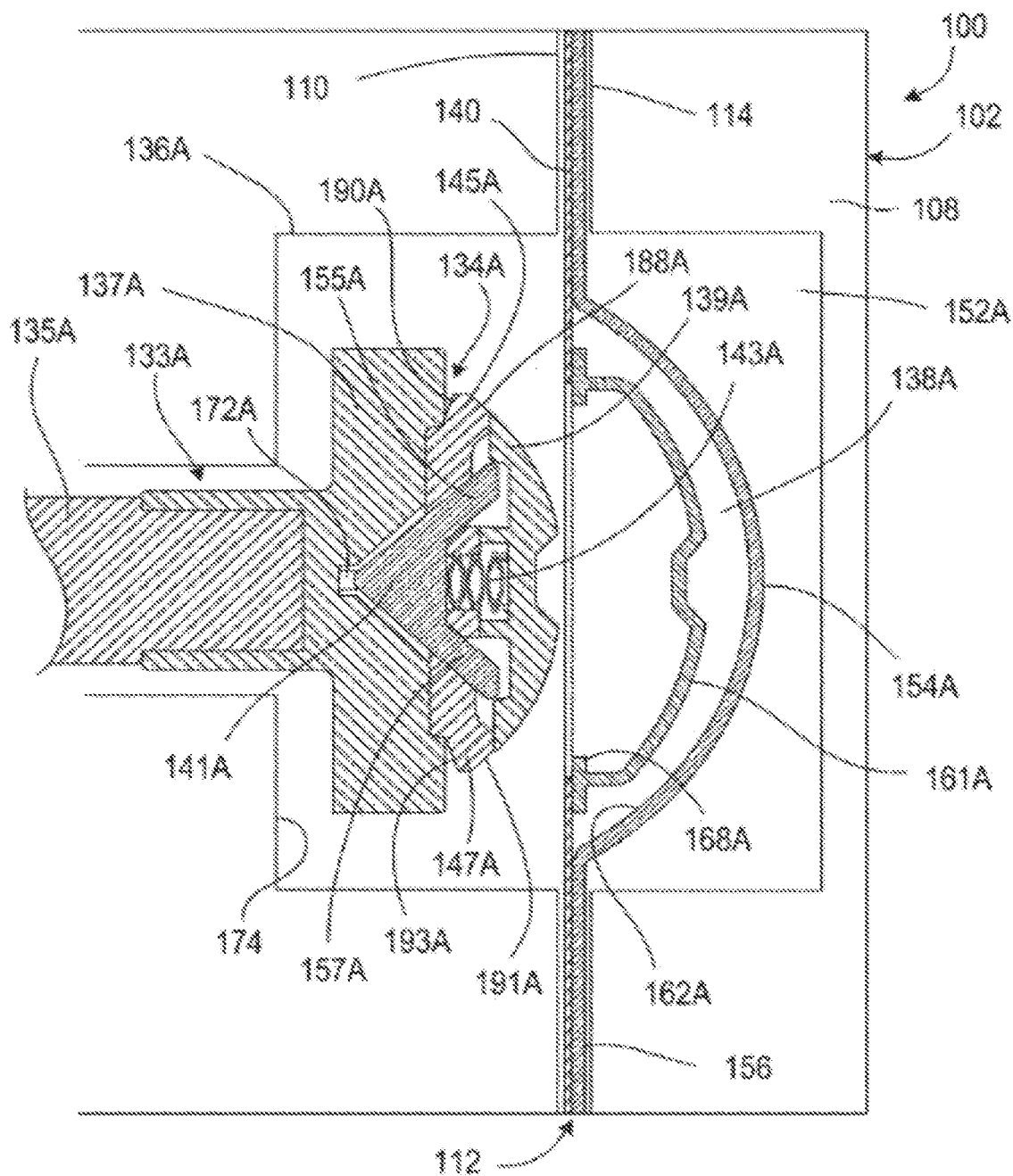
FIGS. 9A-9G are cross-sectional views of the PD system at various stages of setup, priming, and treatment, in accordance with some embodiments.

As depicted in FIG. 9A, the piston 133A is fully retracted into the piston access port 136A of the cassette interface 110. The cassette 112 is positioned in the cassette compartment 114 of the PD machine 102 and the inflatable pad in the door 108 of the PD machine 102 is inflated such that the cassette 112 is pressed tightly against the cassette interface 110 of the PD machine 102.

Figure 9B:
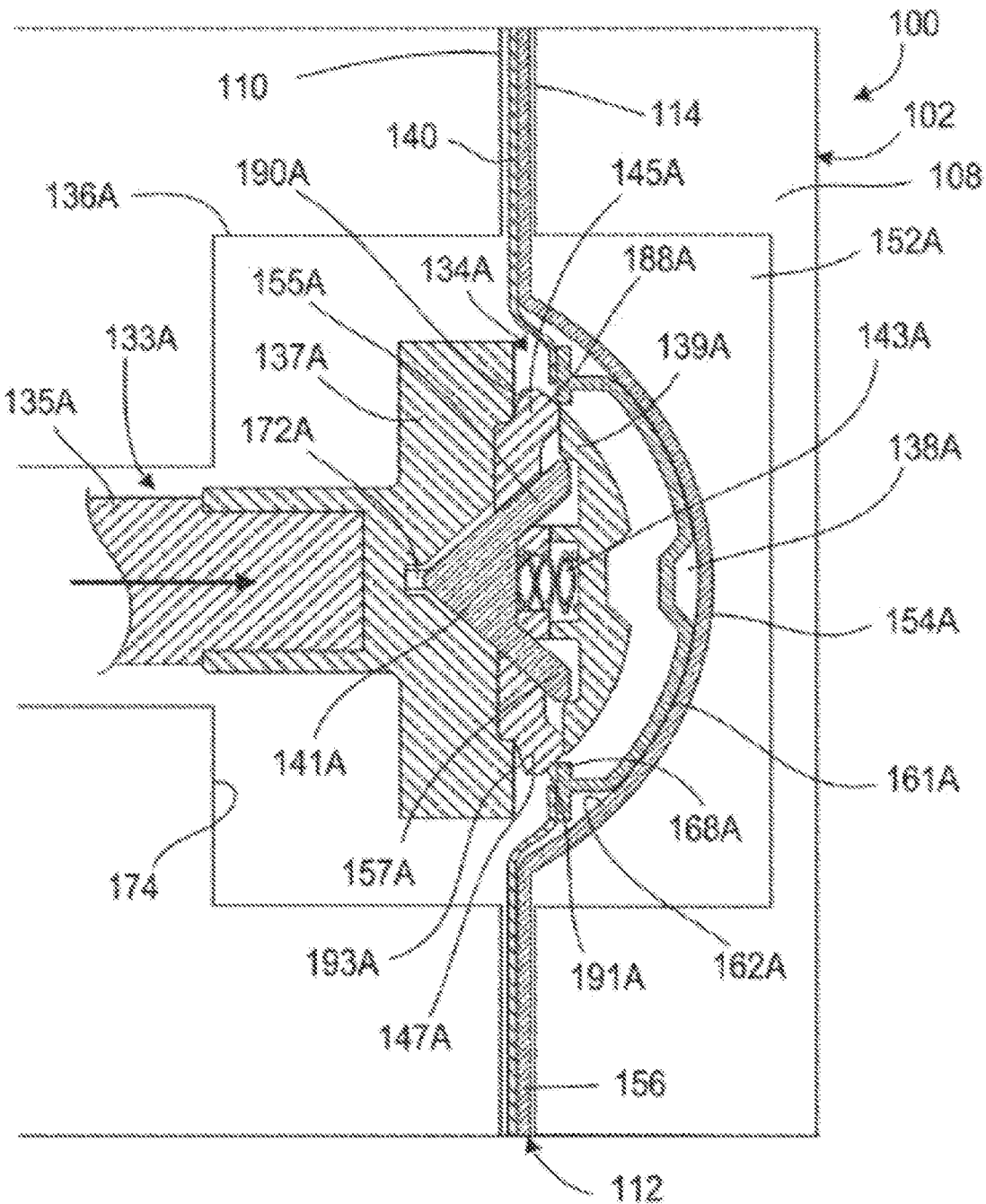

As depicted in FIG. 9B, with the cassette 112 properly installed within the cassette compartment 114 of the PD machine 102 and the appropriate line connections made, the piston 133A is advanced to initiate the process of mechanically connecting the piston head 134A of the PD machine 102 to the dome-shaped fastening member 161A of the cassette 112. As the piston 133A is advanced, a front angled surface 188A of a sliding latch 145A and a front angled surface 191A of a sliding latch 147A contact a rear surface of the annular projection 168A, which extends radially inward from the dome-shaped fastening member 161A. The rear surface of the annular projection 168A is approximately perpendicular to the longitudinal axis of the piston 133A.

As the piston 133A continues to advance, the dome-shaped fastening member 161A contacts the inner surface of the portion of the rigid base 156 that forms the recessed region 162A. The rigid base 156 prevents further forward movement of the dome-shaped fastening member 161A. The membrane 140, which is attached to the peripheral flange 164A of the dome-shaped fastening member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped fastening member 161A, the sliding latches 145A, 147A are caused to move radially inward (e.g., toward the longitudinal axis of the piston 133A) as the piston head 134A continues to be advanced relative to the dome-shaped fastening member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped fastening member 161A. The radial inward movement of each of the sliding latches 145A, 147A in turn causes a forward movement of a latch lock 141A of the piston head 134A due to the mated geometries of the outer surfaces of legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by a spring 143A disposed in a recessed portion of the piston head 134A.

Figure 9C:
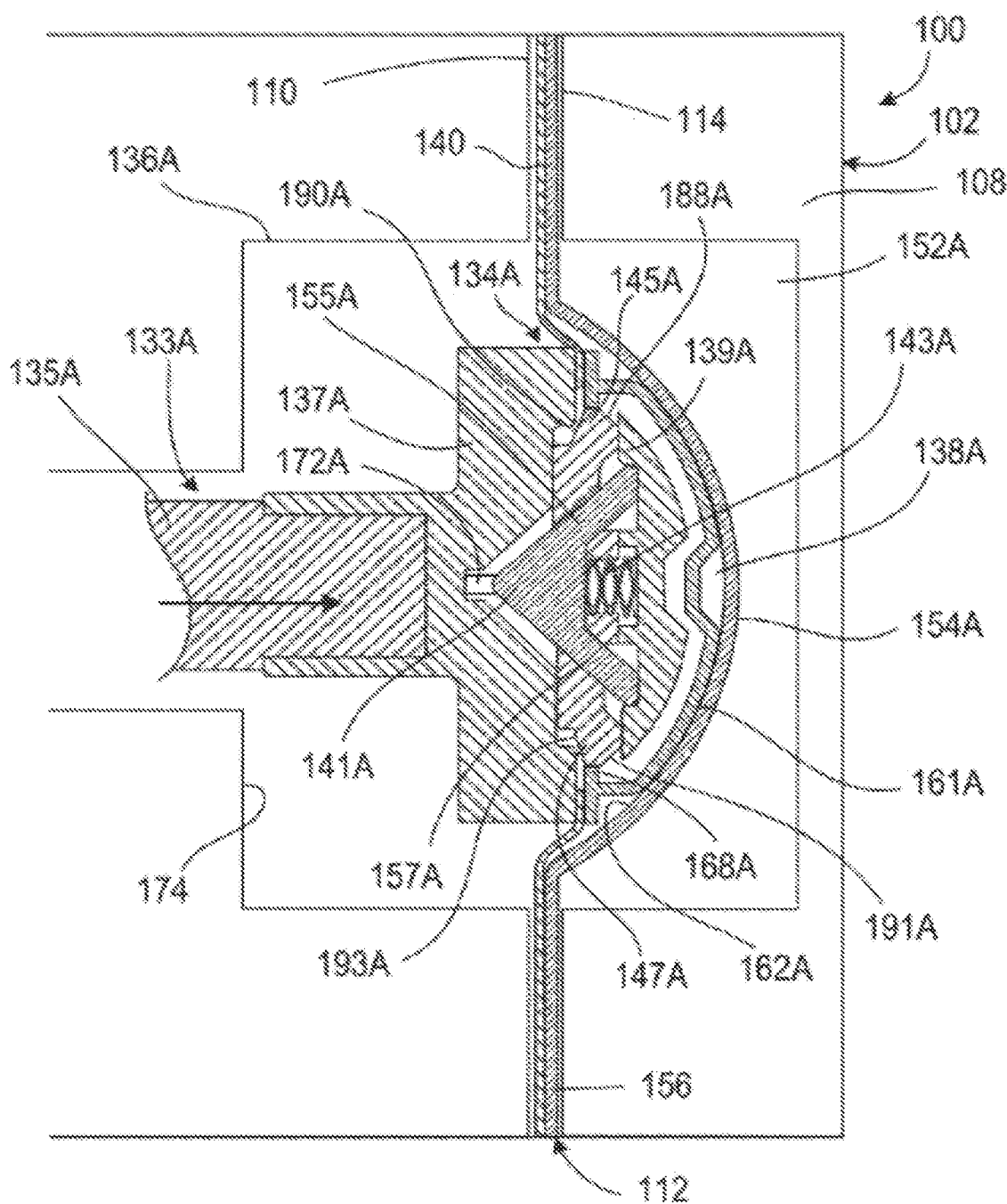

As depicted in FIG. 9C, the piston head 134A is located at a point during the connection process at which the sliding latches 145A, 147A have been deflected radially inward a sufficient distance to allow the sliding latches 145A, 147A to pass beyond the annular projection 168A that extends radially inward from the dome-shaped fastening member 161A. In this position, outer peripheral surfaces of the sliding latches 145A, 147A, which are substantially parallel to the longitudinal axis of the piston 133A, contact and slide along an inner surface of the annular projection 168A of the dome-shaped fastening member 161A, which is also substantially parallel to the longitudinal axis of the piston 133A. The spring 143A is further compressed due to the deflected positions of the sliding latches 145A, 147A.

Figure 9D:
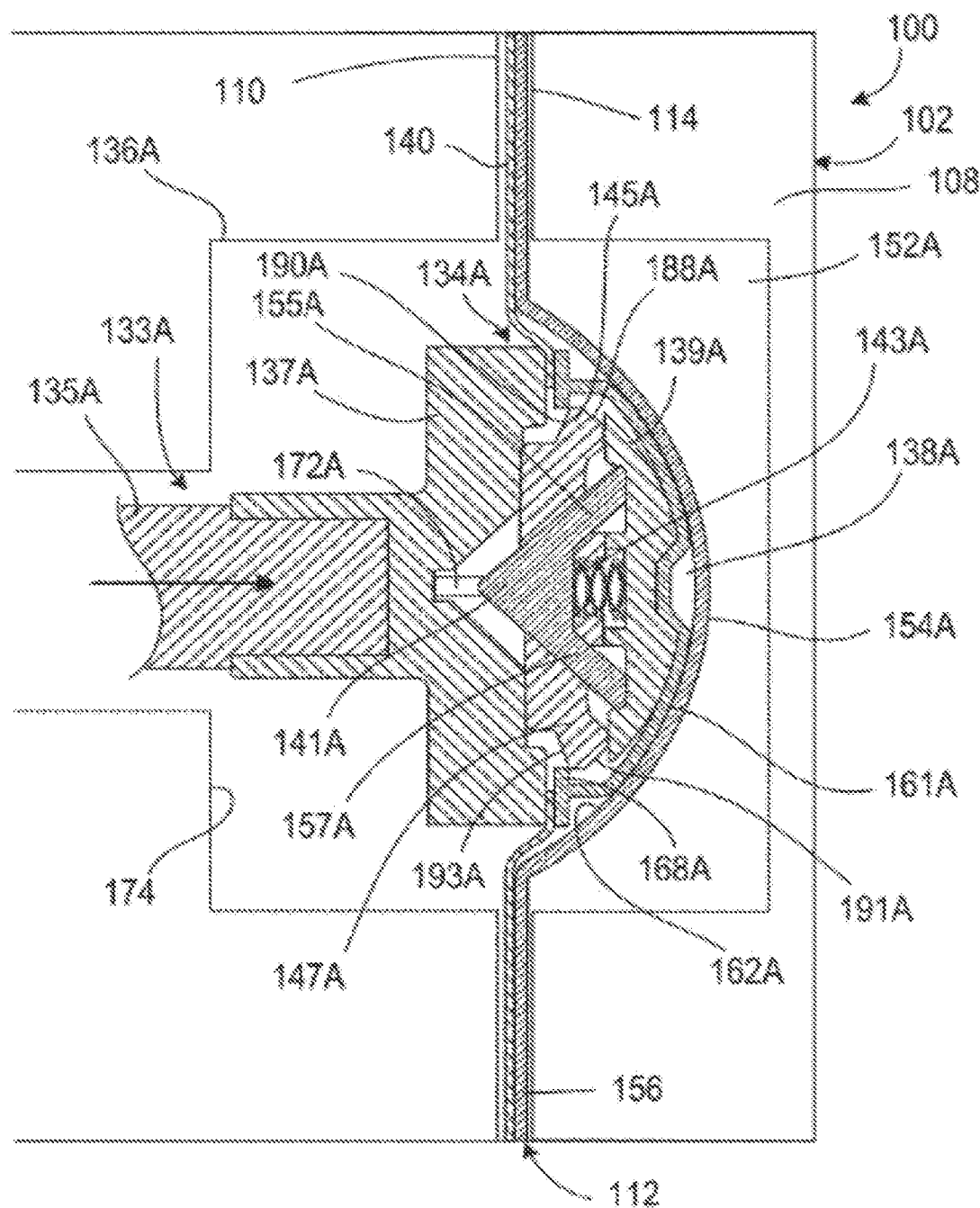

As depicted in FIG. 9D, as the sliding latches 145A, 147A pass beyond the annular projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, thereby causing the sliding latches 145A, 147A to move radially outward underneath the annular projection 168A of the dome-shaped fastening member 161A. Rear angled surfaces 190A, 193A of the sliding latches 145A, 147A ride along the front surface of the annular projection 168A of the dome-shaped fastening member 161A, which is slightly angled toward the rear of the dome-shaped fastening member 161A, as the sliding latches 145A, 147A move radially outward. The sliding latches 145A, 147A become wedged beneath the annular projection 168A as the sliding latches 145A, 147A move radially outward.

Figure 9E:
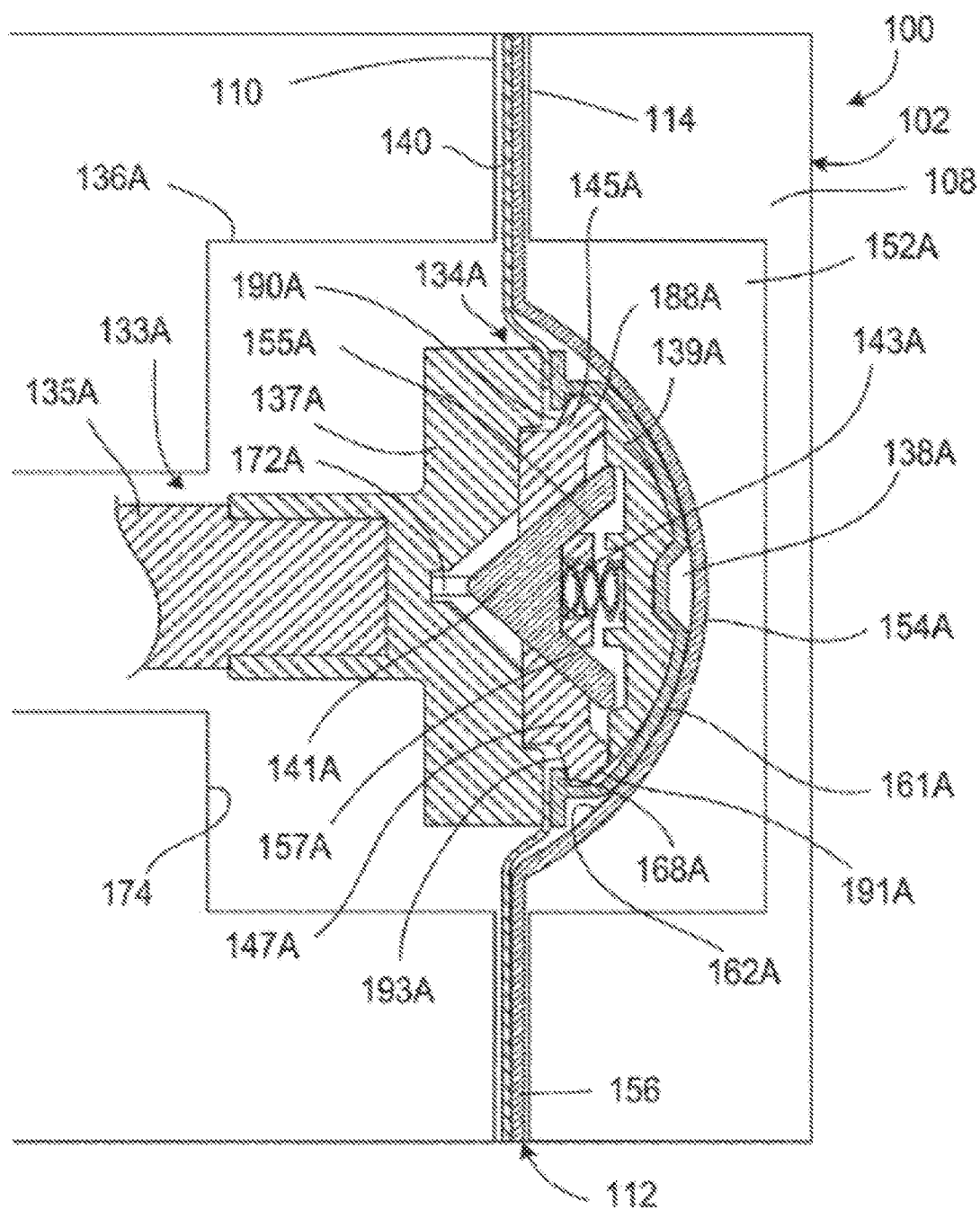

As depicted in FIG. 9E, the piston head 134A and the dome-shaped fastening member 161A are mechanically engaged through a mechanism in which the sliding latches 145A, 147A have moved to maximum outwardly displaced positions within the dome-shaped fastening member 161A on an interior side of the annular projection 168A. In this configuration, the annular projection 168A of the dome-shaped fastening member 161A is effectively pinched between a rear member 137A of the piston head 134A and rear angled surfaces 190A, 193A of the sliding latches 145A, 147A, resulting in a secure mechanical connection between the piston head 134A and the dome-shaped fastening member 161A. As a result of the mechanical engagement of the piston head 134A to the dome-shaped fastening member 161A, the amount of slippage of the piston head 134A relative to the dome-shaped fastening member 161A can be reduced (e g, minimized) and thus precise pumping can be achieved.

After mechanically coupling the piston head 134A of the PD machine 102 to the dome-shaped fastening member 161A of the cassette 112, a priming procedure is carried out to remove air from the cassette 112 and from the various lines 126, 128, 130, and/or 132 connected to the cassette 112. In order to prime the cassette 112 and the lines 126, 128, 130, 132, the piston 133A and inflatable members 142 are typically operated to pump dialysate from the heater bag 124 to the drain and from each of the dialysate bags 122 to the drain. Dialysate is also passed (e.g., by gravity) from the heater bag 124 to the patient line 130 to force any air trapped in the patient line out of a hydrophobic filter positioned at the distal end of the patient line 130.

Figure 9F:
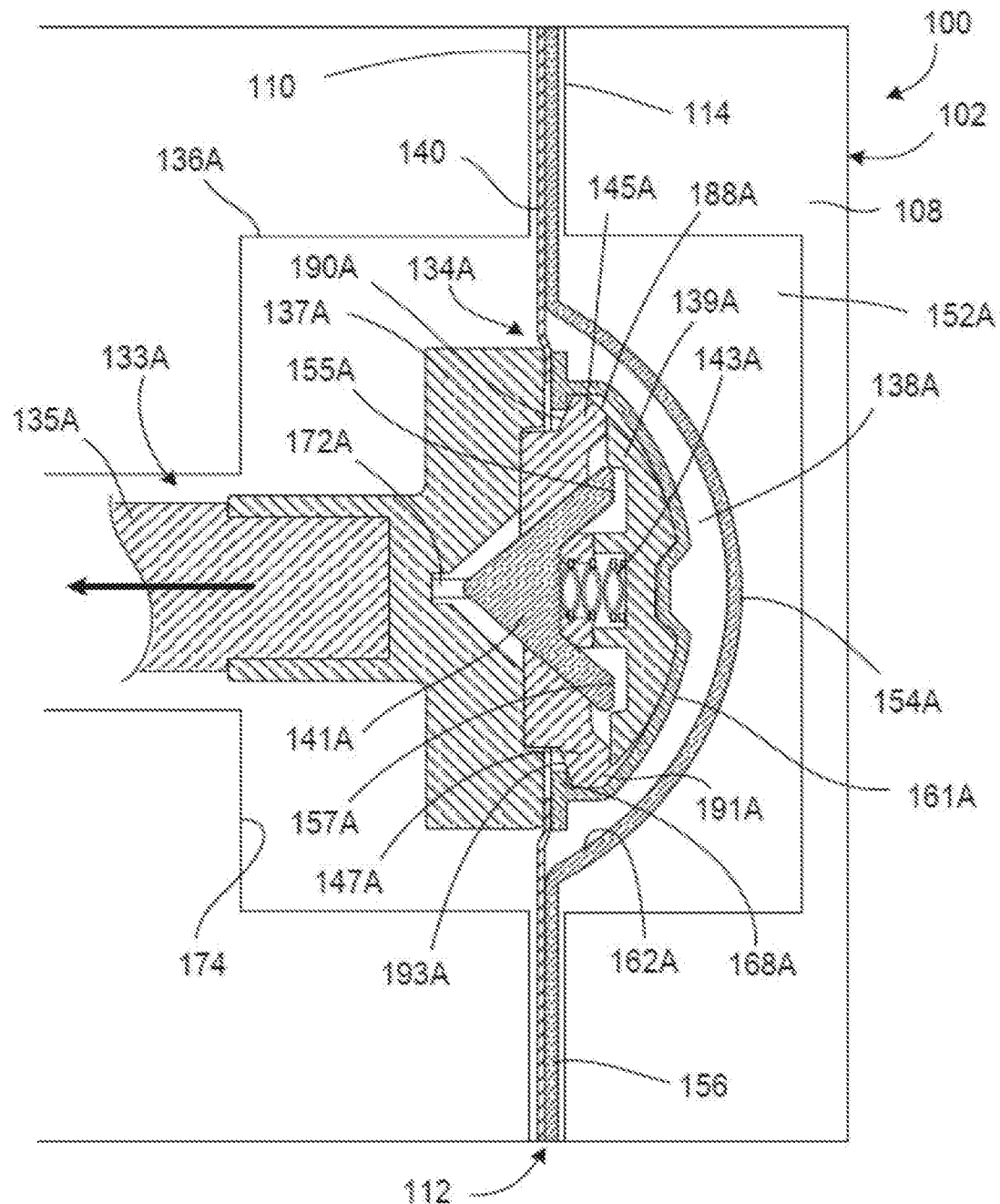

As depicted in FIG. 9F, after the priming procedure is complete, the patient line 130 is connected to the patient and the PD machine 102 is operated to drain any spent dialysate that was left in the patient's peritoneal cavity from a previous treatment. To drain the spent dialysate from the patient's peritoneal cavity, the inflatable members 142 of the PD machine 102 are configured to create an open fluid flow path between the patient line 130 and the port 187A (shown in FIG. 4) fluidly coupled to the pump chamber 138A, and the piston 133A is retracted to draw spent dialysate from the peritoneal cavity of the patient into the pump chamber 138A via the patient line 130. Because the piston head 134A is mechanically connected to the dome-shaped fastening member 161A and the dome-shaped fastening member 161A is attached to the membrane 140 of the cassette 112, the retraction of the piston 133A causes the dome-shaped fastening member 161A and the portion of the membrane 140 attached to the dome-shaped fastening member 161A to move rearward, away from the rigid base 156. As a result, the volume of the pump chamber 138A is increased reducing the pressure of fluid contained therein, and spent dialysate is drawn into the pump chamber 138A from the peritoneal cavity of the patient due to the pressure differential across the distal ends of the patient line 130. The spent dialysate travels from the patient line 130 through the pressure sensing chamber 163A of the cassette 112 and then enters the pump chamber 138A via the port 187A. The pressure sensor 151A monitors the fluid pressure in the pressure sensing chamber 163A, which is approximately equal to the fluid pressure in the pump chamber 138A, during this process.

Figure 9G:
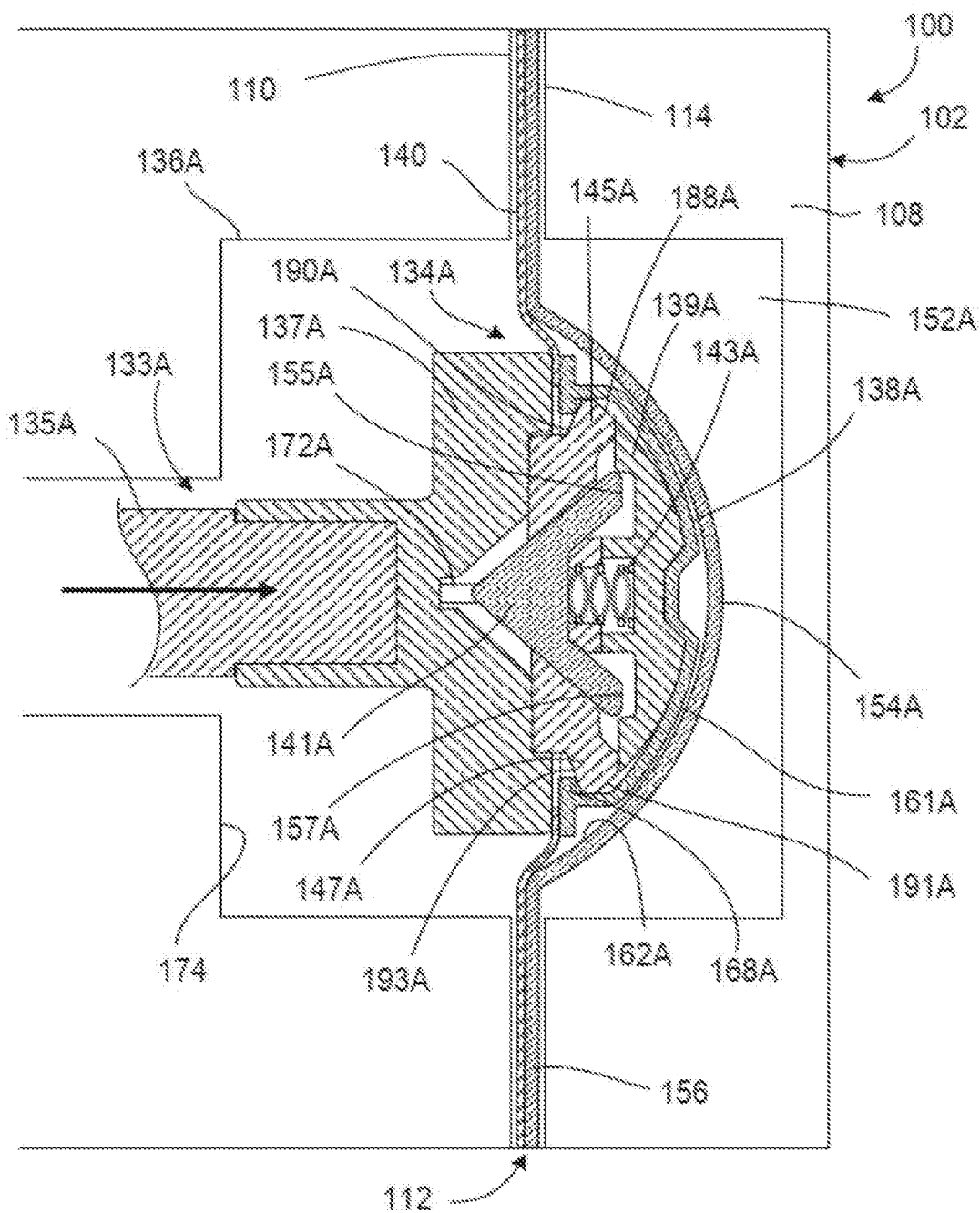

As depicted in FIG. 9G, after drawing the dialysate into the pump chamber 138A from the peritoneal cavity of the patient, the inflatable members 142 of the PD machine 102 are configured to create an open fluid flow path between the port 185A (shown in FIG. 4) fluidly coupled to the pump chamber 138A and the drain line 132, and the piston 133A is advanced to force dialysate out of the pump chamber 138A to the drain or drain receptacle. The piston 133A is typically advanced until the dome-shaped fastening member 161A contacts or nearly contacts the inner surface of the recessed region 162A of the base 156 so that substantially all of the dialysate is forced out of the fluid pump chamber 138A via the port 185A.

During the patient drain phase of the treatment, the pistons 133A, 133B are typically alternately operated such that the piston 133A is retracted to draw spent dialysate solution into the pump chamber 138A from the patient while the piston 133B is advanced to pump spent dialysate solution from the pump chamber 138B to the drain or drain receptacle, and vice versa.

To begin the patient fill phase, the inflatable members 142 are configured to create an open fluid flow path between the pump chamber 138A and the heater bag line 128, and then the piston 133A is retracted, as shown in FIG. 9F, to draw warm dialysate from the heater bag 124 to the pump chamber 138A. The warm dialysate travels from the heater bag 124 through the heater bag line 128 and into the pump chamber via the port 185A.

The warm dialysate is then delivered to the peritoneal cavity of the patient via the patient line 130 by configuring the inflatable members 142 to create an open fluid flow path between the pump chamber 138A and the patient line 130, and then the piston 133A is advanced, as shown in FIG. 9G, to pump warm dialysate to the patient. The warm dialysate exits the pump chamber 138A via the port 187A and travels through the pressure sensing chamber 163A to the patient line 130 before reaching the peritoneal cavity of the patient. The pressure sensor 151A monitors the fluid pressure in the pressure sensing chamber 163A, which is approximately equal to the fluid pressure in the pump chamber 138A, during this process.

During the patient fill phase of the treatment, the pistons 133A, 133B are typically alternately operated such that the piston 133A is retracted to draw warm dialysate into the pump chamber 138A from the heater bag 124 while the piston 133B is advanced to pump warm dialysate from the pump chamber 138B to the patient and vice versa. When the desired volume of dialysate has been pumped to the patient, the machine 102 transitions from the patient fill phase to a dwell phase. During the dwell phase, the dialysate is allowed to sit within the peritoneal cavity of the patient for a long period of time.

During the dwell phase (e.g., a period of time referred to as the dwell period), toxins cross the peritoneum of the patient into the dialysate from the patient's blood. As the dialysate dwells within the patient, the PD machine 102 prepares fresh dialysate for delivery to the patient in a subsequent cycle. In particular, the PD machine 102 pumps fresh dialysate from one of the four full dialysate bags 122 into the heater bag 124 for heating. To do this, the pump of the PD machine 102 is activated to cause the pistons 133A, 133B to reciprocate and certain inflatable members 142 of the PD machine 102 are inflated to cause the dialysate to be drawn into the fluid pump chambers 138A, 138B of the cassette 112 from the selected dialysate bag 122 via its associated line 126. The dialysate is then pumped from the fluid pump chambers 138A, 138B to the heater bag 124 via the heater bag line 128.

After the dialysate has dwelled in the patient for the desired period of time, the spent dialysate is pumped from the patient to the drain line 132 in the manner described above. The heated dialysate is then pumped from the heater bag 124 to the patient where it dwells for a desired period of time. These steps are repeated with the dialysate from two of the three remaining dialysate bags 122. The dialysate from the last dialysate bag 122 is typically delivered to the patient and left in the patient until the subsequent PD treatment.

After completion of the PD treatment, the pistons 133A, 133B are retracted in a manner to disconnect the piston heads 134A, 134B from the dome-shaped fastening members 161A, 161B of the cassette. The door 108 of the PD machine 102 is then opened and the cassette 112 is removed from the cassette compartment 114 and discarded.

Figure 10:
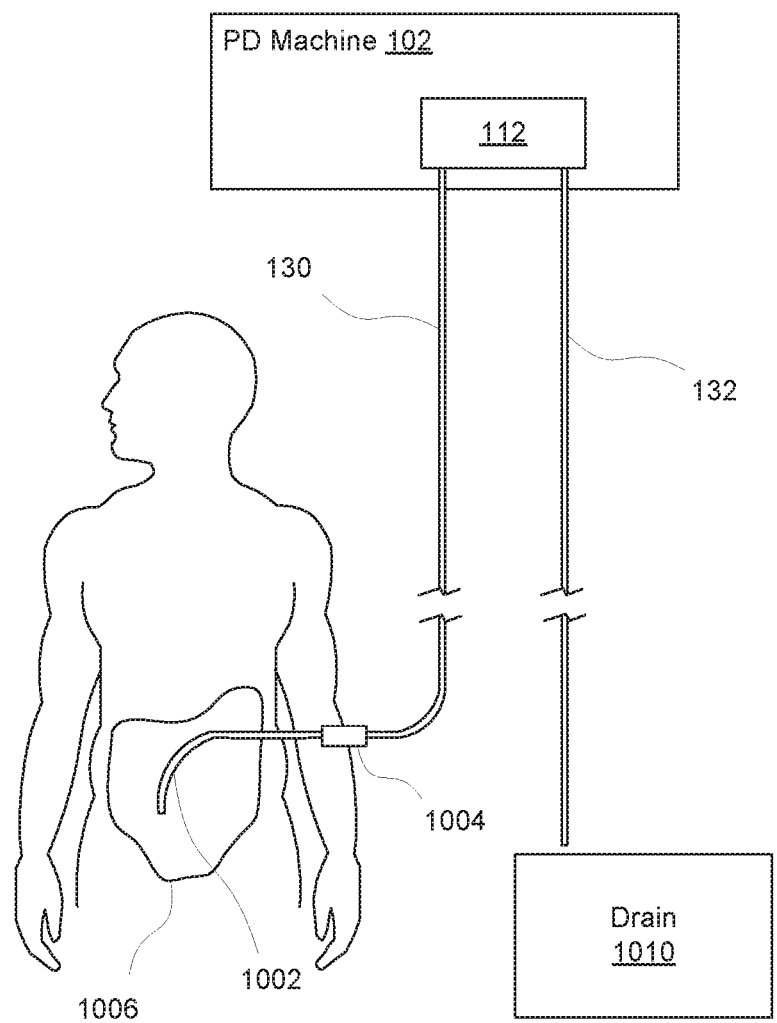
FIG. 10 illustrates a path between the patient and the PD machine when the patient is receiving a PD treatment, in accordance with some embodiments.

FIG. 10 illustrates a path between the patient and the PD machine 102 when the patient is receiving a PD treatment, in accordance with some embodiments. As depicted in FIG. 10, a proximal end of the patient line 130 is connected to the cassette 112 that is installed in the PD machine 102. A distal end of the patient line 130 is connected to the patient's abdomen 1006 via a catheter 1002. The catheter 1002 is connected to the patient line via a port 1004. In some embodiments, the patient line 130 can be a hollow tube formed from distensible and/or flexible material that is at least partially distended by operating pressures in the PD machine 102. In other words, fluid pressure causes the outer walls of the hollow tube to expand radially, thereby enabling the fluid to flow through the center of the tube. For example, in some embodiments, the patient line 130 can be made of an elastomeric material such as a polymer that expands in response to positive operating pressures in the fluid caused by the pumping action of the PD machine 102. The patient line 130, the port 1004, and the catheter 1002 are sometimes referred to as the patient line-catheter conduit, or simply conduit.

It will be appreciated that, during use, at least one of the pump chambers 138A, 138B and pressure sensing chambers 163A, 163B of the cassette 112 are fluidly coupled to the proximal end of the patient line 130 in order to induce fluid (e.g., dialysate solution) to flow through the patient line 130 in response to movement of the pistons 133A, 133B. The pressure sensors 151A, 151B can continuously monitor the fluid pressure in the corresponding pressure sensing chambers 163A, 163B. The signal generated by the pressure sensors 151A, 151B is indicative of the magnitude and direction of the fluid flow into or out of the pump chambers 138A, 138B and, due to a particular configuration of the inflatable members 142, can be indicative of the fluid flow through the patient line 130, drain line 132, dialysate bag lines 126 (not explicitly shown), or heater bag line 128 (not explicitly shown).

As depicted in FIG. 10, a proximal end of the drain line 132 is connected to the cassette 112, and a distal end of the drain line 132 is connected to a drain 1010 or a drain receptacle such as a bag, tub, or other receptacle capable of holding fluid. In some embodiments, the drain line 132 can be a hollow tube formed from distensible and/or flexible material that is at least partially distended by operating pressures in the PD machine 102. In some embodiments, the drain line 132 can be made of an elastomeric material such as a polymer that expands in response to positive operating pressures in the fluid caused by the pumping action of the PD machine 102. It will be appreciated that the distal end of the drain line 132 can be open to the air in order to promote fluid discharge into the drain 1010. Consequently, when fluid flow is unobstructed by occlusions in the drain line 132, the operating pressures in the drain line 132 can be less than the operating pressures in the patient line 130 due to the lower resistance at the distal end of the drain line compared to the distal end of the patient line 130. In some embodiments, the drain line 132 can include a one-way valve, such as a check valve, that prevents backflow of fluid from the drain 1010 to the cassette 112. The one-way valve can also prevent air in the drain line from being introduced into the cassette 112, which can decrease the reliability of readings of the pressure sensors 151A, 151B.

During a PD treatment cycle, an occlusion or blockage can be introduced at different locations in the conduit. For example, the patient line 130 can become pinched or kinked. In addition, pores or ports in the catheter 1002 can become blocked (e.g., clogged with omental fat or other body tissues), or the patient line 130 can develop an internal blockage (e.g., as omental fat moves through the catheter 1002 and port 1004 and is trapped inside the patient line 130).

Figure 11A:
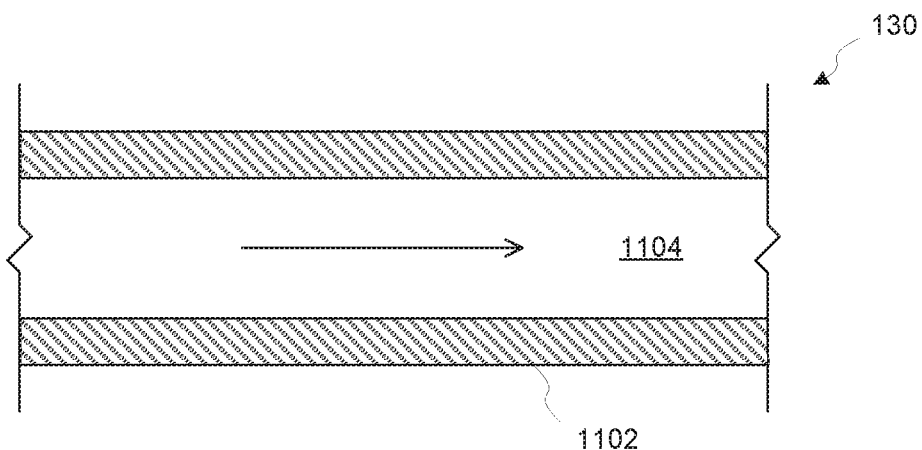
FIGS. 11A-11C illustrate a patient line with various levels of occlusion, in accordance with some embodiments.
Figure 11B:
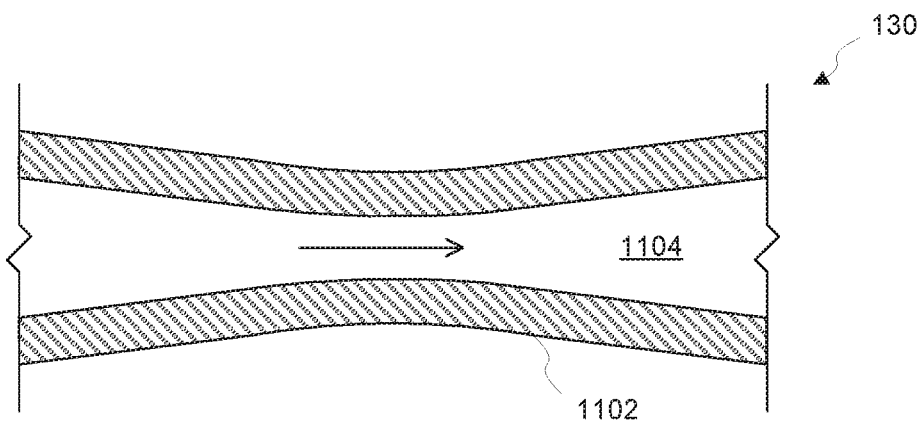
Figure 11C:
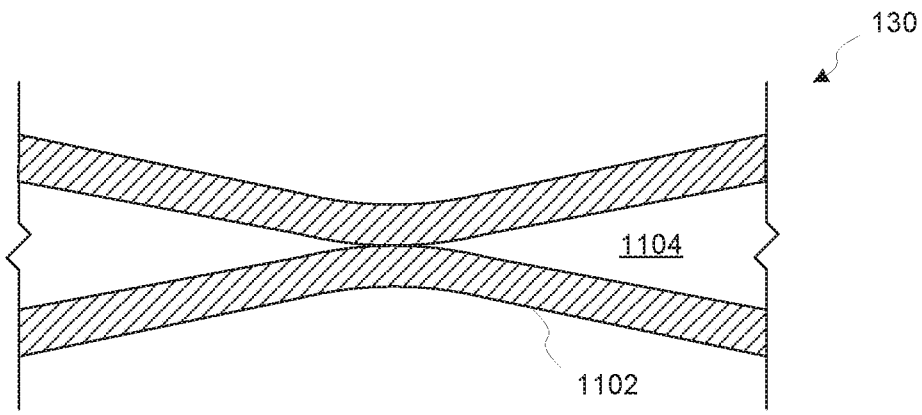

FIGS. 11A-11C illustrate a patient line 130 with various levels of occlusion, in accordance with some embodiments. As depicted in FIG. 11A, during normal operation, the patient line 130 is fully distended allowing fluid to flow freely in the hollow area 1104 between the walls 1102 of the patient line 130. There is no blockage in the patient line 130, and the rate of fluid flow is dependent on the pressure differential between the proximal end and the distal end of the patient line 130. The magnitude of the fluid flow (e.g., the flow rate) is depicted by the length of the arrow shown in the hollow area 1104. In some embodiments, the cross-sectional area of the hollow area 1104 is circular due to a constant thickness of the walls 1102 of the patient line 130 around an axis of the patient line 130 (e.g., symmetrical around the axis).

As depicted in FIG. 11B, the patient line 130 can become pinched, causing a partial occlusion in the patient line 130. For example, the patient can roll over onto the patient line 130, compressing the walls 1102 of the patient line 130 between the patient and a bed or other surface. Alternatively, the patient can set an object, like a book, on top of the patient line 130 where the weight of the object causes a partial collapse of the walls 1102. As the patient line 130 is pinched, a cross-sectional area of the hollow area 1104 is reduced and changes in shape from circular to ovular. Fluid flow is reduced through the smaller cross-sectional area of the hollow area 1104, and a pressure drop is induced across the occluded section of the patient line 130.

As depicted in FIG. 11C, the patient line 130 can become pinched, causing a full occlusion in the patient line 130. While the partial occlusion shown in FIG. 11B restricts but does not fully stop fluid flow through the patient line 130, in some cases the amount of the obstruction can be severe enough to fully block fluid flow through the patient line 130. The cross-section area of the hollow area 1104 can be reduced to zero. Furthermore, suction on the proximal side of the occlusion induced by the pumping action of the pistons 133A, 133B can further fortify the occlusion as the pressure in the proximal side of the patient line 130 drops below atmospheric pressure on the outside of the patient line 130, where atmospheric pressure applies a force on the walls 1002 of the patient line 130 that reinforces the pinching action.

Although FIGS. 11A-11C illustrate a pinch in the patient line 130, similar effects are caused due to a kink where the patient line 130 is bent and the walls 1102 collapse when the bend radius is too severe. A kinked line can also result in a partial occlusion or a full occlusion, depending on the severity of the bend radius at a particular location of the patient line 130.

The PD machine 102 is configured to adjust the operating parameters of the PD machine 102 in an attempt to clear the occlusion and/or to modulate the flow in the patient line 130 to avoid an overpressure condition. In some embodiments, the control unit 139 can be configured to provide an alert indicating that an occlusion has been detected. For example, a visual, tactile, and/or audible alert can be directed to the patient (e.g., to make the patient aware of the condition and/or to wake the patient if the patient is asleep during treatment). In some embodiments, the patient can be alerted multiple times with the severity of the alert increasing over time. For example, a volume of the audible alert can be increased over a period of time or a visual alert (e.g., a blinking light) can be changed to an audible alert after a period of time.

In various embodiments, the PD machine 102 can be configured to automatically attempt to clear the occlusion prior to alerting the patient to the issue. In general, reducing the number of alerts and/or the requirement for a patient to clear an alarm is desirable where the issue can be resolved automatically. In order to determine an appropriate response to a detected condition, the PD machine 102 is configured to ascertain the type of occlusion that is present. In some embodiments, the type of occlusion can be inferred based on the location of the occlusion in the conduit. For example, an occlusion in the conduit at a location associated with the catheter 1002 likely means that the ports of the catheter 1002 are clogged or there is a buildup of fat or other tissue in the catheter 1002. In contrast, an occlusion in the conduit at a location associated with the patient line 130 likely means that the patient line 130 is pinched or kinked.

One technique for measuring the location of the occlusion is to monitor and measure a change in pressure in the patient line 130 as fluid is pumped into or suctioned out of the proximal end of the patient line 130. When there is a full occlusion in the patient line 130, the patient line 130 can be modeled as a cylindrical pressure vessel where the diameter of the cylinder is equal to the inner diameter of the patient line 130. The ratio of the change in volume of the fluid in the line to the change in pressure can be used to infer a length of the pressure vessel and, therefore, a proximate location of the occlusion in the patient line 130. In conventional PD machines 102, when an occlusion is detected in the patient line 130 while the dialysate solution is being drained from the patient's peritoneal cavity, the PD machine 102 can be configured to reverse the flow in the patient line 130 to attempt to clear the occlusion and, potentially, measure the location of the occlusion (e.g., using the technique discussed above). The increase in fluid pressure in the proximal end of the patient line 130 can sometimes cure the condition that caused the occlusion, such as by forcing the patient line 130 to be unkinked or expelling the obstruction back into the peritoneal cavity of the patient. Even if the occlusion remains, the amount of fluid and the pressure increase can provide information to the PD machine 102 about the location of the possible occlusion to provide that information to the patient.

However, reversing the flow of fluid back into the patient is not ideal. First, the dialysate solution being drained from the patient contains waste products that are being removed via the PD treatment. The PD machine 102 should avoid re-introducing the effluent dialysate (e.g., dialysate solution plus waste products) into the patient to prevent these waste products from remaining in the peritoneal cavity after the PD treatment is complete. Second, reversing the flow of the fluid increases the time to drain the patient's peritoneal cavity to prepare for the next PD cycle. Decreasing the total length of the PD treatment by minimizing the PD cycle time is important for a patient's mobility as they can disconnect the patient line 130 from the port 1004 sooner and be free to move on to other activities. Finally, the occlusion might not have the same characteristics when the fluid is flowing in one direction versus the other direction. For example, the occlusion might be located at the connection between the port 1004 and the patient line 130 where foreign objects cannot flow through the orifice at the connection but can move inside the catheter 1002. In another example, a negative pressure differential in the patient line 130 compared to the atmospheric pressure might fully close the hollow area 1004 of a kinked line, but a positive pressure differential may at least partially open the hollow area 1004 at the location of the kink. Consequently, pumping fluid back into the patient line 130 in response to detecting a possible occlusion may not be the preferred response of the PD machine 102.

Figure 12:
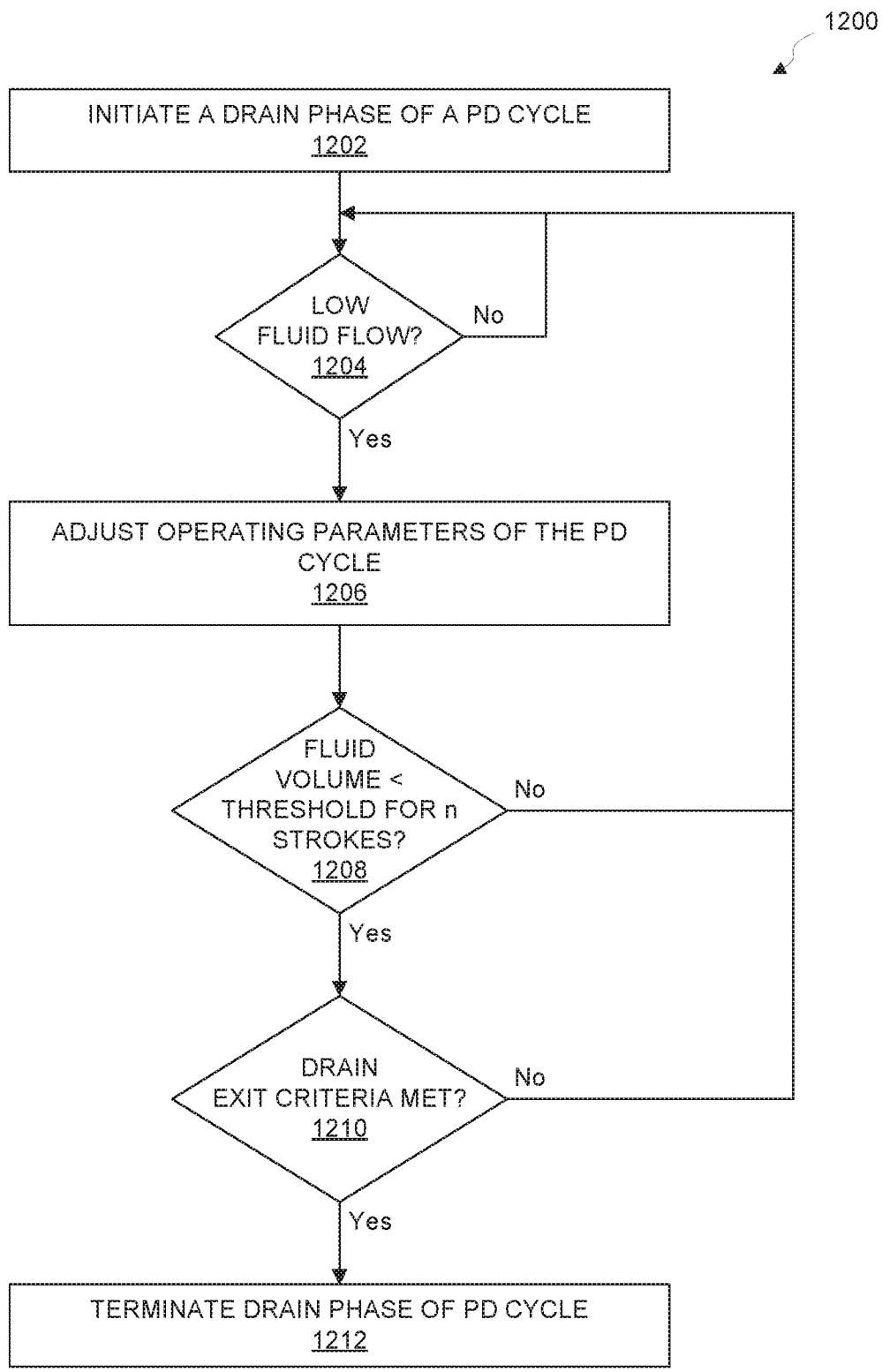
FIG. 12 is a flow diagram of a method for responding to a potential occlusion of the patient line during PD treatment, in accordance with some embodiments.

FIG. 12 is a flow diagram of a method 1200 for responding to a potential occlusion of the patient line during PD treatment, in accordance with some embodiments. It will be appreciated that the method 1200 is described as being performed by the PD system 100. More specifically, the various steps described below can be implemented by a processor, such as the control unit 139 of the PD machine 102, configured to execute a number of instructions. However, it will be appreciated that the method 1200 can be performed by any PD machine configured to drain fluid from a peritoneal cavity of a patient during a PD cycle. In various embodiments, the method 1200 can be implemented using hardware, software executed by a general purpose processor configured to control a specialized apparatus such as a PD machine, or a combination of hardware and software.

At step 1202, a drain phase of a PD cycle is initiated. In some embodiments, the control unit 139 includes a timer that tracks a period of time that a dialysate solution has been contained (i.e., dwelled) in a peritoneal cavity of a patient. The processor compares the period of time tracked by the timer to an operating parameter associated with the PD cycle referred to as a dwell time parameter. If the period of time is greater than or equal to the dwell time parameter, then the drain phase of the PD cycle is initiated.

In some embodiments, the dwell time parameter can be configured manually using the touch screen display 118 and/or the control panel 120. In other embodiments, the dwell time parameter can be set automatically based on prescription information entered by a physician on a network-connected terminal (e.g., a web-based portal of a service maintained by a service provider such as a manufacturer of the PD machine 102) and transmitted to a server. The server can communicate the prescription information to a network interface of the PD machine 102; the processor is then configured to parse the prescription information and set the dwell time.

In yet other embodiments, a patient or caregiver can manually initiate the drain phase of the PD cycle using the touch screen display 118 and/or the control panel 120. This functionality enables a manual override of the dwell time parameter during a specific PD cycle to allow for immediate draining of the patient's peritoneal cavity.

At step 1204, a low fluid flow condition is detected. Normal fluid flow of effluent dialysate from the peritoneal cavity to the drain 1010 can be on the order of 100-200 mL/min. A slow flow rate can be defined as, e.g., 50 mL/min and a low flow rate can be defined as, e.g., 30 mL/min. A low fluid flow condition can refer to total volume of fluid extracted from the patient during the drain phase of the PD cycle, a flow rate per unit time, or an instantaneous volume of fluid pulled into a pump chamber 138A, 138B of the cassette 112 during one or more strokes of the pistons 133A, 133B as compared against a threshold value. The low fluid flow condition can be indicative of, among other causes, an occlusion in the patient line 130.

Figure 13:
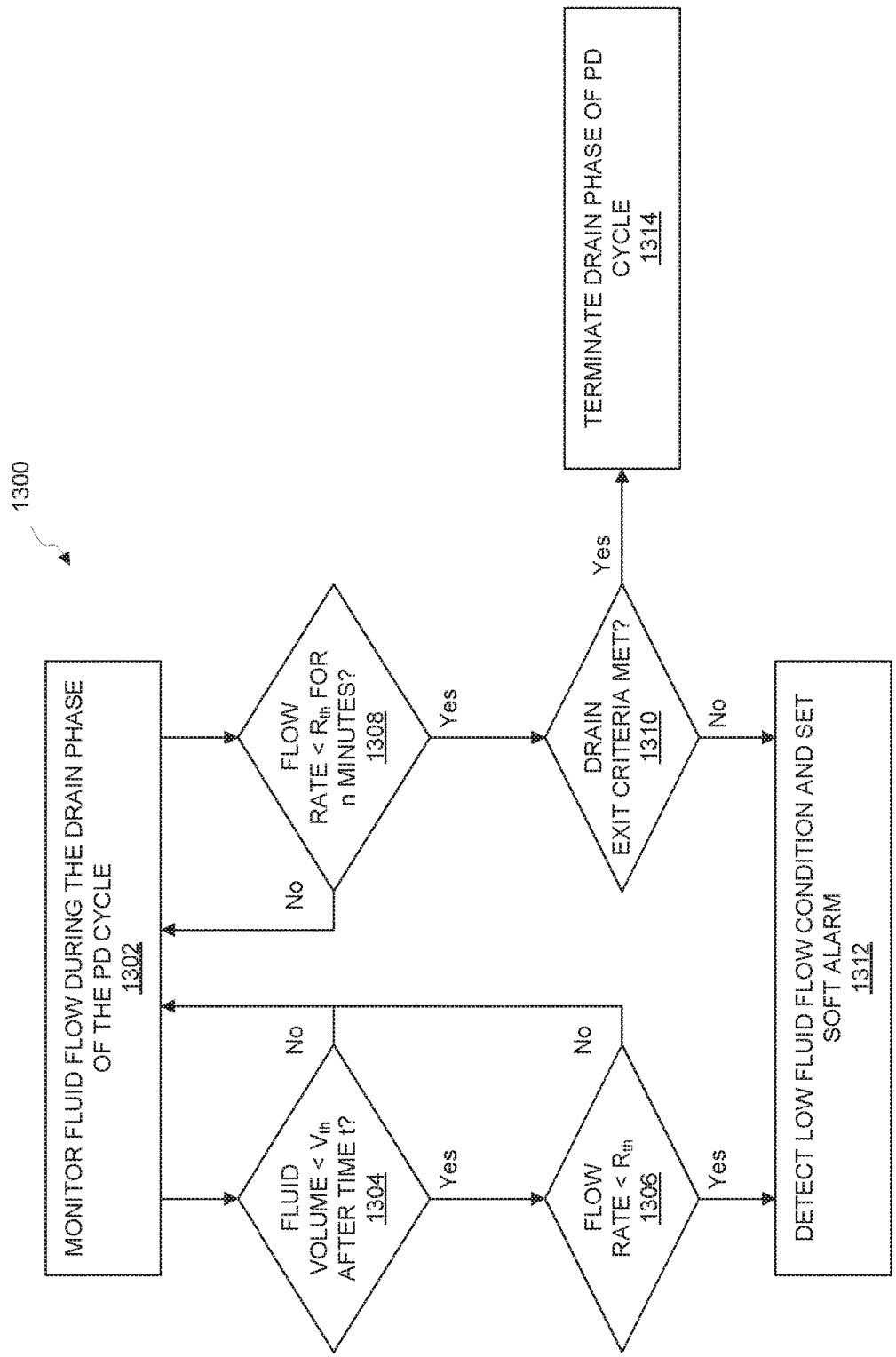
FIG. 13 illustrates a method for detecting a low fluid flow condition, in accordance with some embodiments.

FIG. 13 illustrates a method 1300 for detecting a low fluid flow condition, in accordance with some embodiments. The method 1300 can be performed as part of step 1204 of the method 1200 of FIG. 12.

At step 1302, fluid flow is monitored during a drain phase of a PD cycle. In some embodiments, a fluid pressure signal is tracked by the control unit 139 during each stroke of the pistons 133A, 133B. The fluid pressure signal can refer to a plurality of digital samples of an analog signal, sampled discretely at a particular sampling frequency. In addition to the fluid pressure signal, the control unit 139 can estimate a fluid volume in each of the pump chambers 138A, 138B at the end of each stroke.

In one embodiment, the control unit 139 uses the fluid pressure signal to estimate the fluid volume in each of the pump chambers 138A, 138B. For example, in reference to the first pump chamber 138A, as the piston 133A is retracted into the piston access port 136A fluid is drawn into the first pump chamber 138A. However, if fluid flow is restricted into the first pump chamber 138A and the piston 133A continues to retract, thereby increasing the volume of the first pump chamber 138A, the fluid pressure in the first pump chamber 138A will decrease and/or the membrane 140 or dome-shaped fastening member 161A will be de-coupled from the surface of the piston head 134A. At the end of the full retraction stroke, the piston 133A can be moved forward toward the cassette 112 and the fluid pressure signal can be monitored. The position of the piston head 133A at a point where the fluid pressure begins to increase in the pressure sensing chamber 163A, which is fluidly coupled with the pump chamber 138A, can be used to infer the fluid volume in the pump chamber 138A due to the fluid being incompressible. Because air is compressible, the rate of change in the fluid pressure in the pump chamber 138A will change drastically when the volume of the pump chamber 138A is reduced below the volume of fluid in the pump chamber 138A in the case where there is air in the system. By analyzing the fluid pressure signal, the control unit 139 can infer the fluid volume in the pump chamber 138A and calculate the flow rate by comparing the total volume of fluid passing through the pump chamber 138A with a cycle time of the pumping mechanism.

For example, a volume of the pump chamber 138A over the course of a full stroke of the piston 133A can change from, e.g., <0.1 mL to ~2.0 mL. It will be appreciated that the volumes given here are approximate and can vary based on the design of the cassette 112 or the length of the stroke of the piston 133A. Thus, each retraction stroke of the piston 133A from fully extended to fully retracted can pull a volume of fluid into the pump chamber 138A that matches a difference between the maximum volume of the pump chamber 138A and the minimum volume of the pump chamber 138A. In this example, the volume of fluid pulled into the pump chamber can be approximately 1.9-2.0 mL.

As depicted in FIG. 13, the flow of method 1300 includes multiple branches that can operate in parallel. In other words, the control unit 139 can execute multiple processes either sequentially, where the control unit 139 processes the different branches in a time division multiplexed manner, as needed, or in parallel using, e.g., a multi-core processor.

In a first branch of the flow of method 1300, at step 1304, the control unit 139 determines whether a total fluid volume withdrawn from the patient line 130 after a time, t, is less than a threshold volume. In some embodiments, different low fluid flow conditions are defined at step 1304 that utilize different criteria. In one embodiment, the first low fluid flow condition can be met when a total volume of fluid drained from the peritoneal cavity during the drain phase of the PD cycle is less than 35% of a volume of dialysate inserted into the peritoneal cavity during a fill phase of the PD cycle after at least half (e.g., 50%) of an expected drain period has elapsed. The expected drain period can be estimated based on the amount of dialysate pumped into the patient's peritoneal cavity during the fill phase of the PD cycle or at the end of the last PD treatment, in the case of the initial drain phase of the PD treatment. In another embodiment, the first low fluid flow condition can be met when a total volume of fluid drained from the peritoneal cavity during the drain phase of the PD cycle is less than 70% of a volume of dialysate inserted into the peritoneal cavity during a fill phase of the PD cycle after at least an expected drain period (e.g., 100% of the expected drain period) has elapsed.

In some embodiments, the first low fluid flow condition can be met when a total volume of fluid drained from the peritoneal cavity during the drain phase of the PD cycle is less than 35% of a volume of dialysate inserted into the peritoneal cavity during a fill phase of the PD cycle after at least half of an expected drain period has elapsed or a total volume of fluid drained from the peritoneal cavity during the drain phase of the PD cycle is less than 70% of a volume of dialysate inserted into the peritoneal cavity during a fill phase of the PD cycle after at least an expected drain period has elapsed. It will be appreciated that multiple criteria can be defined at any number of points in time throughout the expected drain period or even beyond the expected drain period (e.g., if the drain phase takes longer than expected due to unusual low flow rates).

If the total fluid volume withdrawn from the patient line 130 after a time, t, is not less than the threshold volume, then the method 1300 returns to step 1302 and continues to monitor fluid flow during normal operation of the drain phase of the PD cycle. However, if the total fluid volume withdrawn from the patient line 130 after a time, t, is less than the threshold volume, then the method proceeds to step 1306, where the control unit 139 determines whether the current fluid flow rate is less than a threshold fluid flow rate. In some embodiments, the fluid flow rate is given in units of volume per unit time, such as milliliters per minute (mL/min), and the threshold fluid flow rate is set at approximately 30 milliliters per minute (mL/min). It will be appreciated that different embodiments can set the threshold fluid flow rate to be greater or less than 30 mL/min.

In some embodiments, the fluid flow rate is determined by measuring the volume of fluid drawn into the pump chamber (s) 138A, 138B during a last retraction stroke of the piston(s) 133A, 133B. The volume of fluid is then divided by a cycle time for both a retraction stroke (to pull fluid into the pump chamber(s) 138A, 138B) and an extension stroke (to push fluid out of the pump chamber(s) 138A, 138B and towards the drain line 132). The cycle time can be measured by a timer. It will be appreciated that, where multiple pistons operate concurrently, the cycle times for one piston can overlap the cycle times for another complementary piston, and the total cycle time is calculated as the total time elapsed while all pistons complete one stroke.

In other embodiments, the fluid flow rate is calculated as a moving average over the last x number of piston cycles, where a piston cycle refers to the total time to perform a retraction stroke followed by an extension stroke for one or more pistons, including any dwell time to, e.g., estimate a volume of fluid drawn into the pump chamber(s) 138A, 138B between the retraction stroke and the extension stroke. Typical fluid flow rates during normal operation are between 100-200 mL/min and cycle times can be on the order of 500-2000 milliseconds. For example, the fluid flow rate can be calculated as the average flow rate over the last 5 piston cycles by summing the volume of fluid in the pump chamber (s) 138A, 138B after each of the 5 retraction strokes and dividing by the time to complete all 5 piston cycles.

If the current fluid flow rate is not less than the threshold fluid flow rate, then the method 1300 returns to step 1302 and continues to monitor fluid flow during normal operation of the drain phase of the PD cycle. However, if the current fluid flow rate is less than the threshold fluid flow rate, then the method proceeds to step 1312, where the low fluid flow condition is detected and a soft alarm is set.

Returning now to step 1302, the second branch of the flow of method 1300 is described with reference to step 1308, where the control unit 139 determines whether the current fluid flow rate is less than a threshold fluid flow rate for the last n minutes. It will be appreciated that the calculation in step 1308 is different in scope than the calculation in step 1306. For example, the current flow rate can refer to an instantaneous fluid flow rate based on as small as a one or more (e.g., 5) strokes of the piston(s) 133A, 133B after a total elapsed time of a number of seconds (e.g., less than 10 seconds), whereas the condition set forth in step 1308 requires a sustained fluid flow rate below the threshold value for a set period of time, such as 3 minutes, which can be much longer than the duration for the calculation of the instantaneous fluid flow rate.

In an embodiment, the threshold fluid flow rate is approximately 30 mL/min. It will be appreciated that the threshold fluid flow rate is not required to be the same as the threshold fluid flow rate of step 1306. For example, step 1308 could utilize a slow fluid flow rate of 50 mL/min whereas step 1306 could use a low fluid flow rate of 30 mL/min. In other words, due to lengthened time that the fluid flow rate must be sustained below the threshold value, a relaxed threshold value can be implemented.

In some embodiments, step 1308 does not require the fluid flow rate to be sustained below the threshold fluid flow rate for the entire duration of the n minutes. In other words, as long as the average fluid flow rate over the n minutes is below the threshold fluid flow rate, the condition for step 1308 is met.

If the current fluid flow rate is not less than the threshold fluid flow rate for the last n minutes, then the method 1300 returns to step 1302 and continues to monitor fluid flow during normal operation of the drain phase of the PD cycle. However, if the current fluid flow rate is less than the threshold fluid flow rate for the last n minutes, then the method proceeds to step 1310, where the control unit 139 determines whether a drain exit criteria is met. The drain exit criteria refers to a set of one or more conditions or rules for terminating the drain phase of the PD cycle early. Examples of the drain exit criteria can include the existence of a hard alarm, an elapsed time of the drain phase of the PD cycle above a threshold time (e.g., 110% of expected drain period), or a total volume of dialysate drained from the patient above a threshold value based on a volume of dialysate pumped into the peritoneal cavity during a previous fill phase of the PD cycle.

If the drain exit criteria is met, then the method proceeds to step 1314, where the drain phase of the PD cycle is terminated. In some embodiments, the PD treatment will continue with the next cycle. In some cases, such as the existence of a hard alarm, the PD treatment will stop temporarily while waiting for the patient or caregiver to service one or more alerts/alarms.

However, if at step 1310 the drain exit criteria is not met, then the method 1300 proceeds to step 1312, where the low fluid flow condition is detected and a soft alarm is set. A more complete description of an alarm handling routine is described below in reference to FIG. 14.

Returning now to FIG. 12, at step 1204, if the low fluid flow condition is not detected, the drain phase continues using the normal operating parameters, including operating the at least one pump, in one embodiment, at a first speed (e.g., linear speed) or first rate (e.g., cycle time). However, if the low fluid flow condition is detected, then, at step 1206, operating parameters of the PD cycle are adjusted. In some embodiments, the operating parameters are adjusted to reduce a speed of the at least one pump from the first speed to a second speed that is less than the first speed. For example, if the pistons 133A, 133B are configured during normal operating conditions to change position at a speed of, e.g., 500 mils/second (0.5 inches per second), then the operating parameters can be adjusted to reduce the speed of the pistons to, e.g., 100 mils/second or 20% of the normal operating speed.

It will be appreciated that the speed of the pistons 133A, 133B may not be linear throughout the entire stroke, or can be different in the retraction stroke versus the extension stroke. In some embodiments, the operating parameters can be adjusted to change the motion profile of the pistons 133A, 133B such that reducing the speed of the pistons 133A, 133B refers to reducing the overall time to complete a retraction stroke rather than an instantaneous linear speed of the pistons 133A, 133B at a particular point in time. For example, in some embodiments, the speed of the pistons 133A, 133B can remain the same when comparing, e.g., the frequency of stepper motor steps sent to the motor drivers during a change in position of the pistons 133A, 133B. However, the total motion profile can be interrupted at multiple points during the retraction stroke (e.g., at 10% increments of the retraction stroke) where the stepper motor maintains a given position (e.g., dwells) in order to lengthen the overall time to complete the full retraction stroke.

In some embodiments, reducing the speed of the pistons 133A, 133B can refer to changing the gain values of, e.g., a proportional-integral-derivative (PID) controller such that the motion profile generated by the PID controller is less aggressive when compared to the initial gain values. In general, there are a variety of ways to adjust the operating parameters of a control system that affect the operation of the pumping mechanism to make the pumping action slower or less aggressive, thereby allowing a longer time for fluid to flow through the patient line 130 and into the pump chambers 138A, 133B in response to the drop in fluid pressure in the pump chambers 138A, 138B caused by the retracting pistons 133A, 133B.

At step 1208, the control unit 139 determines whether the volume of fluid in the pump chambers 138A, 138B after each retraction stroke is less than a threshold fluid volume for the last n strokes. Again, the volume of fluid in the pump chambers 138A, 138B can be estimated using, e.g., the fluid pressure signal and/or the encoder signal. In one embodiment, the threshold fluid volume can be 1.5 mL and the number of strokes is at least 4 consecutive retraction strokes. It will be appreciated that measurement performed at step 1208 is reflective of the pumping mechanism operating at the reduced speed of the adjusted operating parameters and not the higher speed of the normal operating parameters.

If the volume of fluid is not less than a threshold fluid volume for the last n strokes, then the method 1200 returns to step 1204, where the operating parameters are changed back to the normal operating parameters and the drain phase of the PD cycle continues until the next low fluid flow condition is detected. In other embodiments, the method 1200 can return to step 1208 and continue to operate at the reduced speed using the adjusted operating parameters for a period of time (e.g., for a minute) or for a number of additional strokes (e.g., for 50 strokes) before returning to step 1204 if the condition at step 1208 is not satisfied during that time.

However, if the volume of fluid is less than a threshold fluid volume for the last n strokes, then the method 1200 proceeds to step 1210, where the control unit 139 determines whether a drain exit criteria is met. Again, the drain exit criteria refers to a set of one or more conditions or rules for terminating the drain phase of the PD cycle early. If the drain exit criteria is met, then the method proceeds to step 1212, where the drain phase of the PD cycle is terminated.

However, if, at step 1210, the drain exit criteria is not met, then the method 1200 returns to step 1204, where the operating parameters are changed back to the normal operating parameters and the drain phase of the PD cycle continues until the next low fluid flow condition is detected. In other embodiments, the method 1200 can return to step 1208 and continue to operate at the reduced speed using the adjusted operating parameters for a period of time (e.g., for a minute) or for a number of additional strokes (e.g., for 50 strokes) before returning to step 1204 if the condition at step 1208 is not satisfied during that time.

It will be appreciated that the terms "less than" or "greater than," as used above, can encompass "less than or equal to" or "greater than or equal to," respectively, and that the decision of whether the comparison is inclusive or exclusive of the threshold value is merely a design choice unless otherwise clearly contradicted by the context.

Furthermore, the methods 1200 and 1300 are described within the context of the control unit 139 of the PD machine 102. However, in some embodiments, the methods 1200 and 1300 can be implemented, at least in part, by other processors or logic units in addition to or in lieu of the control unit 139, such as a CPU, GPU, system-on-chip (SoC), embedded microcontroller, programmable logic controller, or an apparatus that incorporates such processor or logic units along with other digital or analog circuits on, e.g., a printed circuit board or other substrate.

Figure 14:
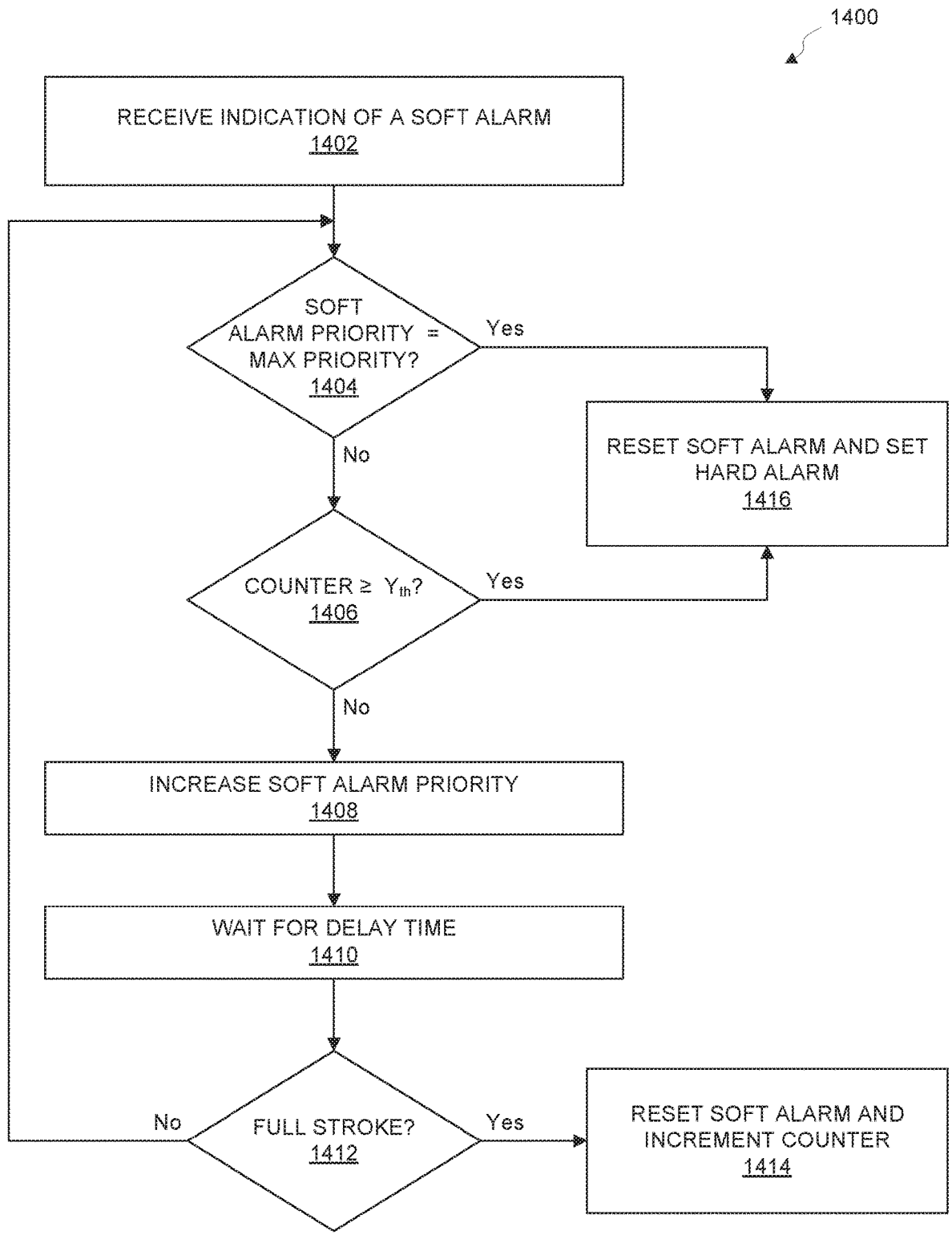
FIG. 14 is a flow diagram of a method for handling soft alarms of the PD machine, in accordance with some embodiments.

FIG. 14 is a flow diagram of a method 1400 for handling soft alarms of the PD machine 102, in accordance with some embodiments. It will be appreciated that the method 1400 is described as being performed by the PD system 100. More specifically, the various steps described below can be implemented by a processor, such as the control unit 139 of the PD machine 102, configured to execute a number of instructions. However, it will be appreciated that the method 1400 can be performed by any PD machine configured to drain fluid from a peritoneal cavity of a patient during a PD cycle. In various embodiments, the method 1400 can be implemented using hardware, software executed by a general purpose processor configured to control a specialized apparatus such as a PD machine, or a combination of hardware and software.

At step 1402, an indication of a soft alarm is received. In some embodiments, the control unit 139 can set a flag or call a routine when a soft alarm is set by a different process or routine, such as step 1312 of method 1300. In response to the soft alarm being set, an alarm handling routine is initiated by, e.g., the control unit 139 or another processor.

At step 1404, the control unit 139 determines whether a current priority of the soft alarm is equal to a maximum priority. As used herein, the priority can refer to a seriousness of the soft alarm and can be set, initially, by the routine that caused the soft alarm. In one embodiment, a low fluid flow condition causes the control unit 139 to set the soft alarm with a minimum priority.

If the current priority for the soft alarm is not equal to the maximum priority, then the method 1400 proceeds to step 1406, where the control unit 139 determines whether a counter is greater than or equal to a threshold value. The counter is a mechanism for tracking how many times the soft alarm has been reset without alerting the patient or caregiver via a hard alarm, as will be described in more detail below. The initial value of the counter is zero.

If the counter is not greater than or equal to the threshold value, then the method 1400 proceeds to step 1408, where the priority of the soft alarm is increased. In one embodiment, the soft alarm priority corresponds to a volume of an audible alert. For example, a minimum priority of 0 corresponds with a muted audible alert. A priority of 1 corresponds with a first volume of the audible alert, a priority of 2 corresponds with a second volume of the audible alert, and so forth up to the maximum volume of the audible alert. In some embodiments, the soft alarm priority corresponds to an alert mode. As used herein, an alert mode can refer to operating parameters for one or more feedback mechanisms that alert the patient or caregiver to an alarm. For example, a first alert mode can refer to a visual cue alone such as a LED located on the PD machine or a message displayed on the touch screen display 118. A second alert mode can refer to both the visual cue and a tactile feedback such as a vibrator motor. A third alert mode can refer to the visual cue and tactile feedback in combination with an audible alert at low volume, and a fourth alert mode can refer to the visual cue and tactile feedback in combination with an audible alert at high volume.

In some embodiments, in response to an increase in priority of the soft alarm, the control unit 139 can operate one or more components of the PD machine 102 to provide the visual cues, tactile feedback, or audible alerts to the patient or caregiver. For example, the control unit 139 can cause a sound such as a beep or audio clip to be played via a speaker of the PD machine 102. The sound can be repeated periodically while the soft alarm is set. In some embodiments, different sounds or audio files can be played depending on the priority of the soft alarm. For example, a short beep can be played for low priority soft alarms whereas a language alert can be played for high priority soft alarms.

At step 1410, the control unit 139 waits for a delay time. In some embodiments, the delay time is at least 60 seconds. During the delay time, the drain phase of the PD cycle can continue and is not interrupted by the soft alarm.

At the end of the delay time, the method 1400 proceeds to step 1412, where the control unit 139 determines whether the next retraction stroke of the pistons 133A, 133B is a full stroke. As used herein, a full stroke can refer to a volume of fluid in the pump chambers 138A, 138B that is greater than a threshold volume. For example, if the maximum volume of the pump chambers 138A, 138B at full retraction of the pistons 133A, 133B is 2.0 mL, then the threshold value can be, e.g., in the range of 1.5-1.9 mL.

If the next retraction stroke is a full stroke, then, at step 1414, the soft alarm is reset and the counter value is incremented. The method 1400 then terminates and the drain phase of the PD cycle continues. It will be appreciated that the counter value counts how many times the soft alarm is triggered and then reset if the full stroke is achieved. The counter value is essentially used to trigger a hard alarm when the flow rate fluctuates too many times because the corrective action of the PD machine 102 is not curing the low fluid flow condition.

Returning to step 1412, if the next retraction stroke is not a full stroke, then the method 1400 returns to step 1404, where the soft alarm priority is compared against the maximum priority value. If, at step 1404, the soft alarm priority is equal to the maximum priority, meaning the soft alarm priority has been incremented one or more times at step 1408 before being reset, then the method 1400 proceeds to step 1416, where a hard alarm is set and the soft alarm is reset. The hard alarm can refer to an alarm that meets one of the drain exit criteria discussed above. In some embodiments, setting the hard alarm will immediately cause the drain phase of the PD cycle to stop until the patient or caregiver manually clears or resets the hard alarm.

Returning to step 1406, if the counter value is greater than or equal to the threshold value, then the method 1400 also proceeds to step 1416. Again, while the criteria of step 1404 requires the priority of a particular soft alarm to be escalated without reaching a full stroke of the pistons 133A, 133B up to the maximum priority value in order to set a hard alarm, the criteria of step 1406 merely requires a number of soft alarms to be set and then reset, thereby indicating an intermittent low fluid flow condition that is at least partially alleviated by the corrective action of the PD machine 102.

In one embodiment, the maximum priority is equal to 7 and the soft alarm priority can be increased from priority values 1, 3, and 7, in increasing order, over the course of 3 minutes corresponding to a delay time of 60 seconds. In another embodiment, the threshold value for the counter is equal to 3 and the number of times a soft alarm can be set and reset is equal to 3 before a hard alarm is triggered at the next occurrence of a soft alarm. In other embodiments, these parameters can be adjusted to change how aggressively soft alarms are escalated into a hard alarm.

Figure 15:
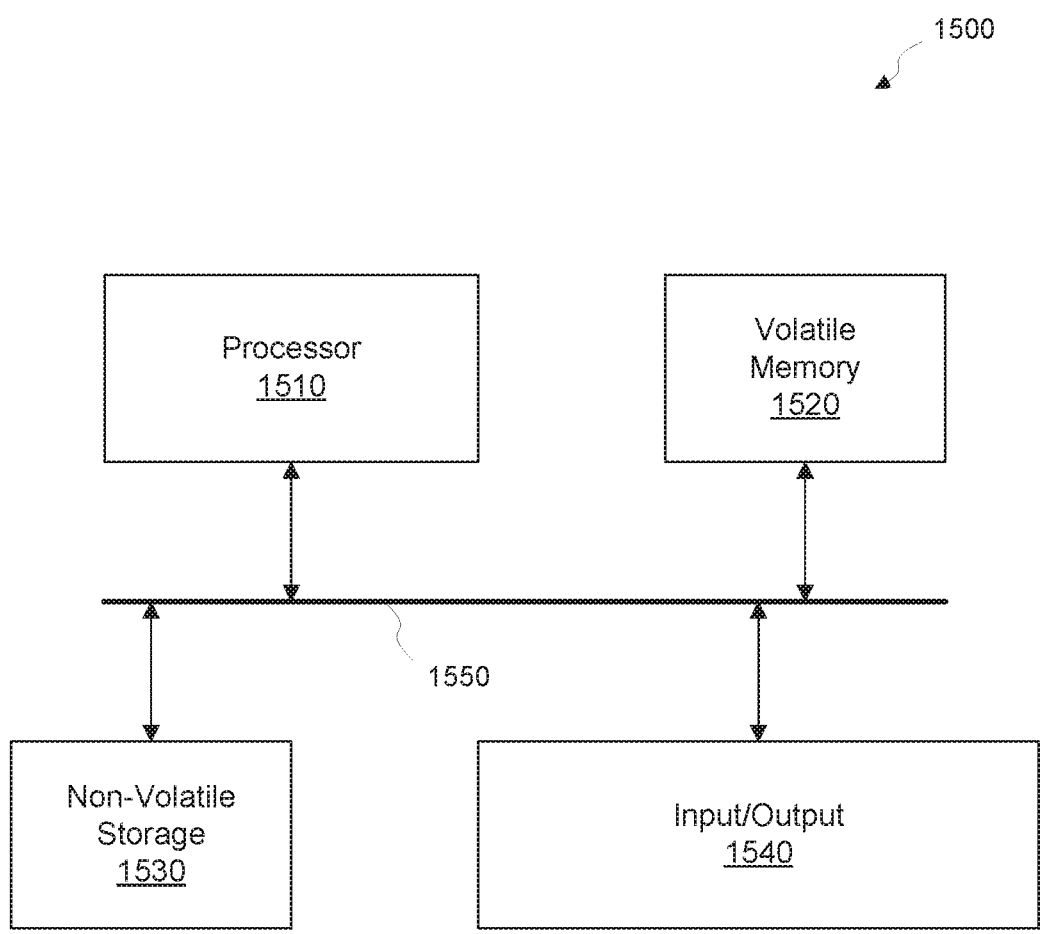
FIG. 15 illustrates an exemplary computer system, in accordance with some embodiments.

FIG. 15 illustrates an exemplary computer system 1500, in accordance with some embodiments. It will be appreciated that, in various embodiments, the control unit 139 can be implemented, at least in part, to include the components of the computer system 1500. The processor 1510 can execute instructions that cause the computer system 1500 to implement the functionality of the control unit 139, as described above.

As depicted in FIG. 15, the system 1500 includes a processor 1510, a volatile memory 1520, a non-volatile storage 1530, and one or more input/output (I/O) devices 1540. Each of the components 1510, 1520, 1530, and 1540 can be interconnected, for example, using a system bus 1550 to enable communications between the components. The processor 1510 is capable of processing instructions for execution within the system 1500. The processor 1510 can be a single-threaded processor, a multi-threaded processor, a vector processor that implements a single-instruction, multiple data (SIMD) architecture, a quantum processor, or the like. The processor 1510 is capable of processing instruction stored in the non-volatile memory 1520. In some embodiments, the non-volatile memory 1520 is a dynamic random access memory (DRAM). The instructions can be loaded into the volatile memory 1520 from the non-volatile storage 1530. In some embodiments, the non-volatile storage 1530 can comprise a flash memory such as an EEPROM. In other embodiments, the non-volatile storage 1530 can comprise a hard disk drive (HDD), solid state drive (SSD), or other types of non-volatile media. The processor 1510 is configured to execute the instructions, which cause the PD machine 102 to carry out the various functionality described above.

In some embodiments, the memory 1520 stores information for operation of the PD machine 102. For example, the operating parameters can be stored in the memory 1520. The processor 1510 can read the values of the operating parameters from the memory 1520 and then adjust the operation of the PD machine 102 accordingly. For example, a speed of the pistons 133A, 133B can be stored in or written to the memory 1520 and read from the memory 1520. The speed is then used to control signals transmitted to the stepper motor drivers.

The I/O device(s) 1540 provides input and/or output interfaces for the system 1500. In some embodiments, the I/O device(s) 1540 include a network interface controller (NIC) that enables the system 1500 to communicate with other devices over a network, such as a local area network (LAN) or a wide area network (WAN) such as the Internet. In some embodiments, the non-volatile storage 1530 can include both local and remote computer readable media. The remote computer readable media can refer to a network storage device such as a storage area network (SAN) or a cloud-based storage service. The I/O device(s) 1540 can also include, but are not limited to, a serial communication device (e.g., RS-232 port, USB host, etc.), a wireless interface device (e.g., a transceiver conforming to Wi-Fi or cellular communication protocols), a sensor interface controller, a video controller (e.g., a graphics card), or the like.

It will be appreciated that the system 1500 is merely one exemplary computer architecture and that the control unit 139 or other processing devices can include various modifications such as additional components in lieu of or in addition to the components shown in FIG. 15. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 1540 functionality when connected to the SoC via a printed circuit board.

Figure 16A:
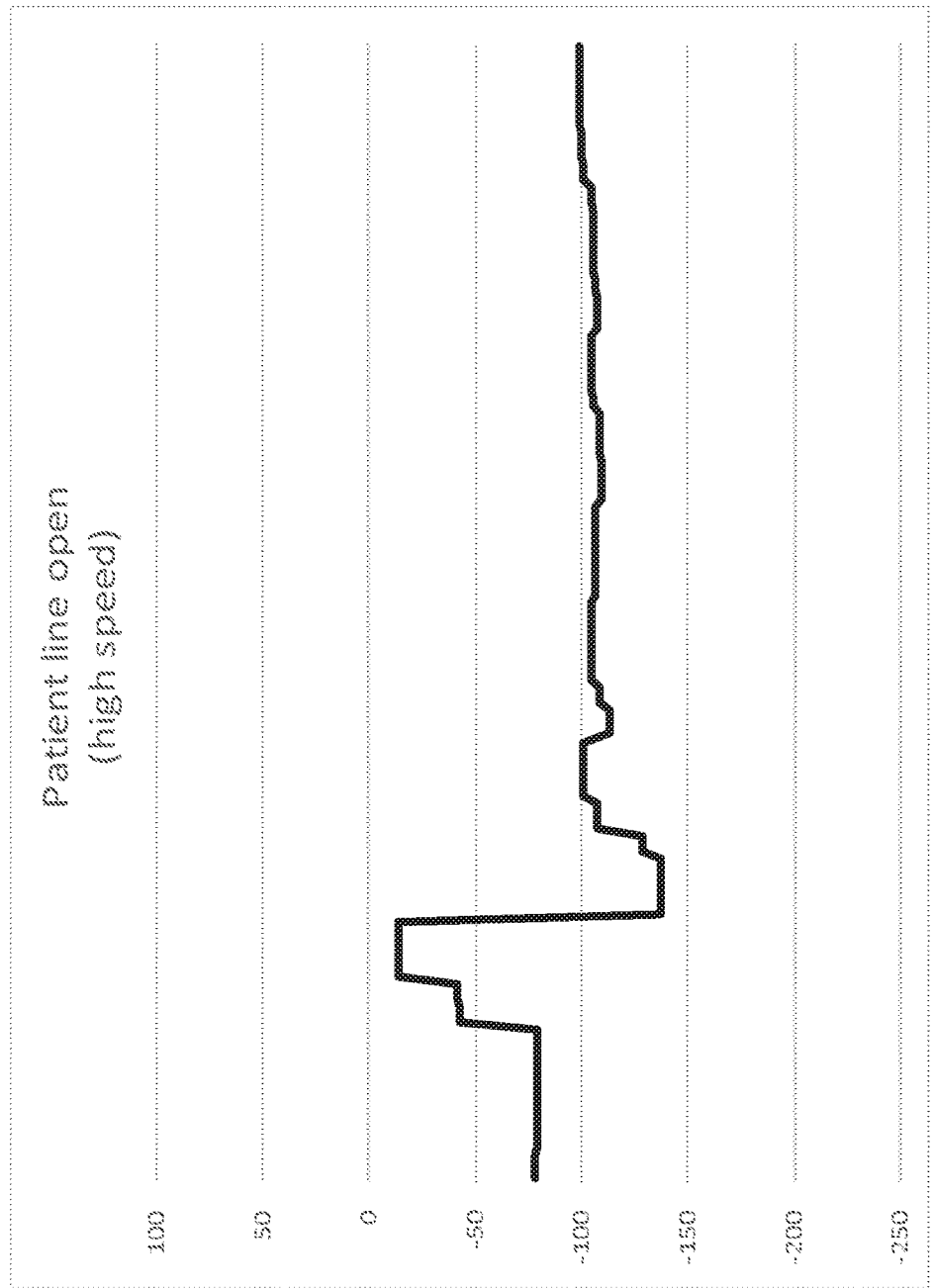
FIGS. 16A-16F illustrate pressure sensor signals during various operations of the PD system, in accordance with some embodiments
Figure 16B:
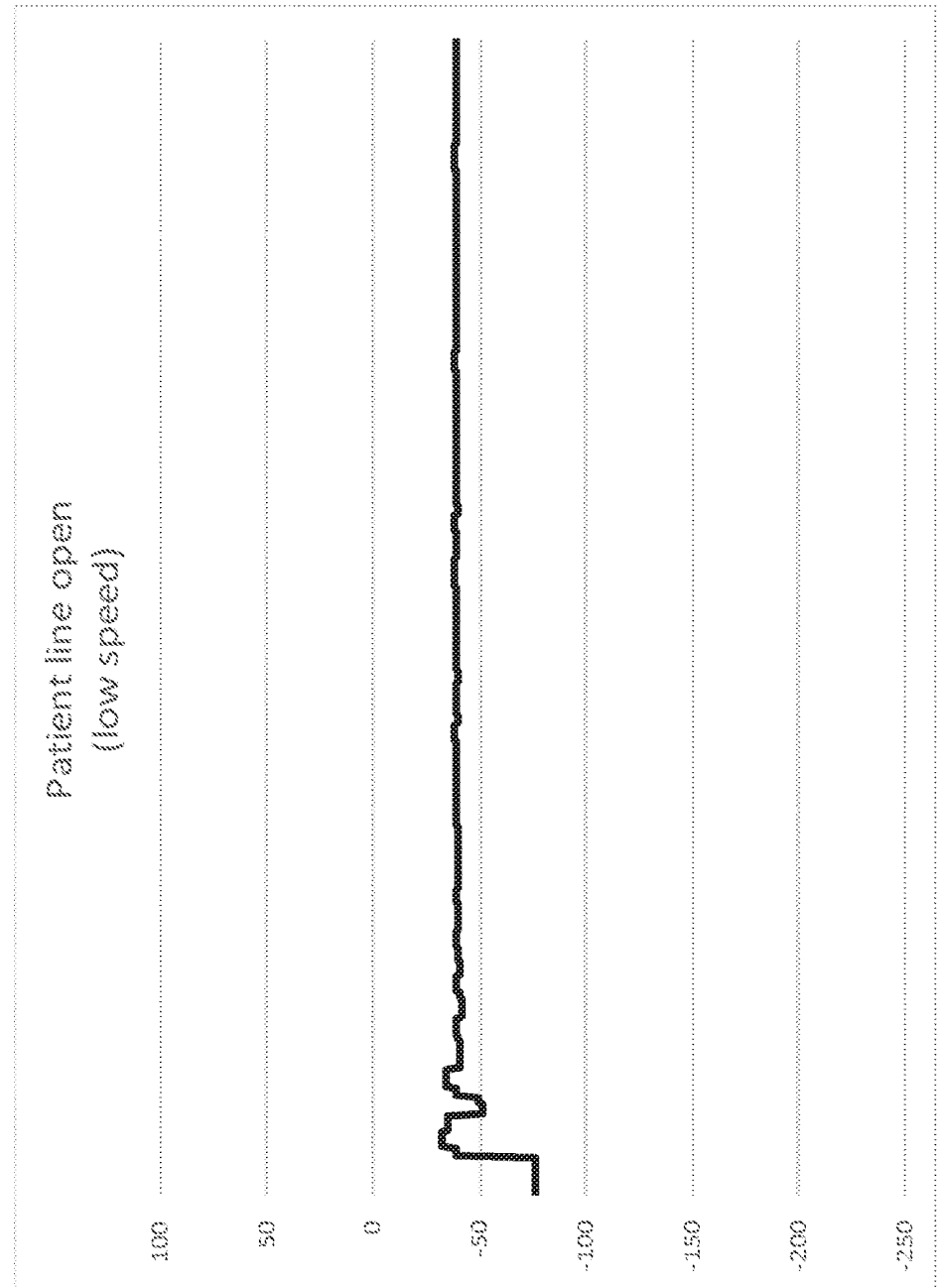

FIGS. 16A-16F illustrate pressure sensor signals during various operations of the PD system 100, in accordance with some embodiments. FIGS. 16A and 16B depict the pressure sensor signal generated during normal operation of a drain phase of a PD cycle with the patient line 130 open (i.e., not occluded). It will be appreciated that the vertical axis shows millibars of pressure relative to atmospheric pressure and the horizontal axis shows time. The horizontal axis is not labeled as the time period for the charts vary. As shown in FIG. 16A, the time period spans approximately 150 seconds for a high speed operation and the steady state pressure while draining effluent dialysate from the patient is approximately −100 mbar. As shown in FIG. 16B, the time period spans approximately 500 seconds for a low speed operation and the steady state pressure while draining effluent dialysate from the patient is approximately −40 mbar.

Figure 16C:
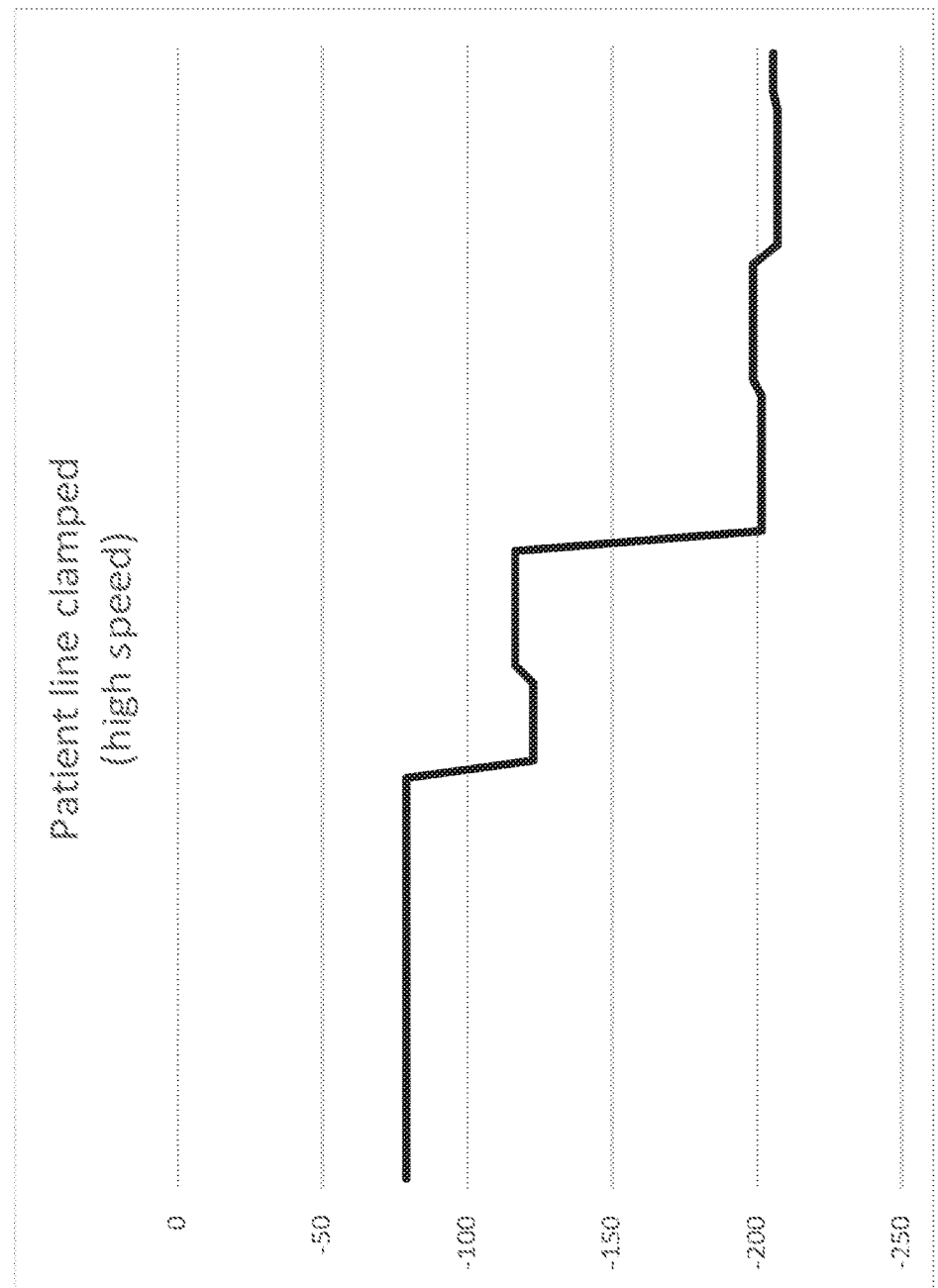
Figure 16D:
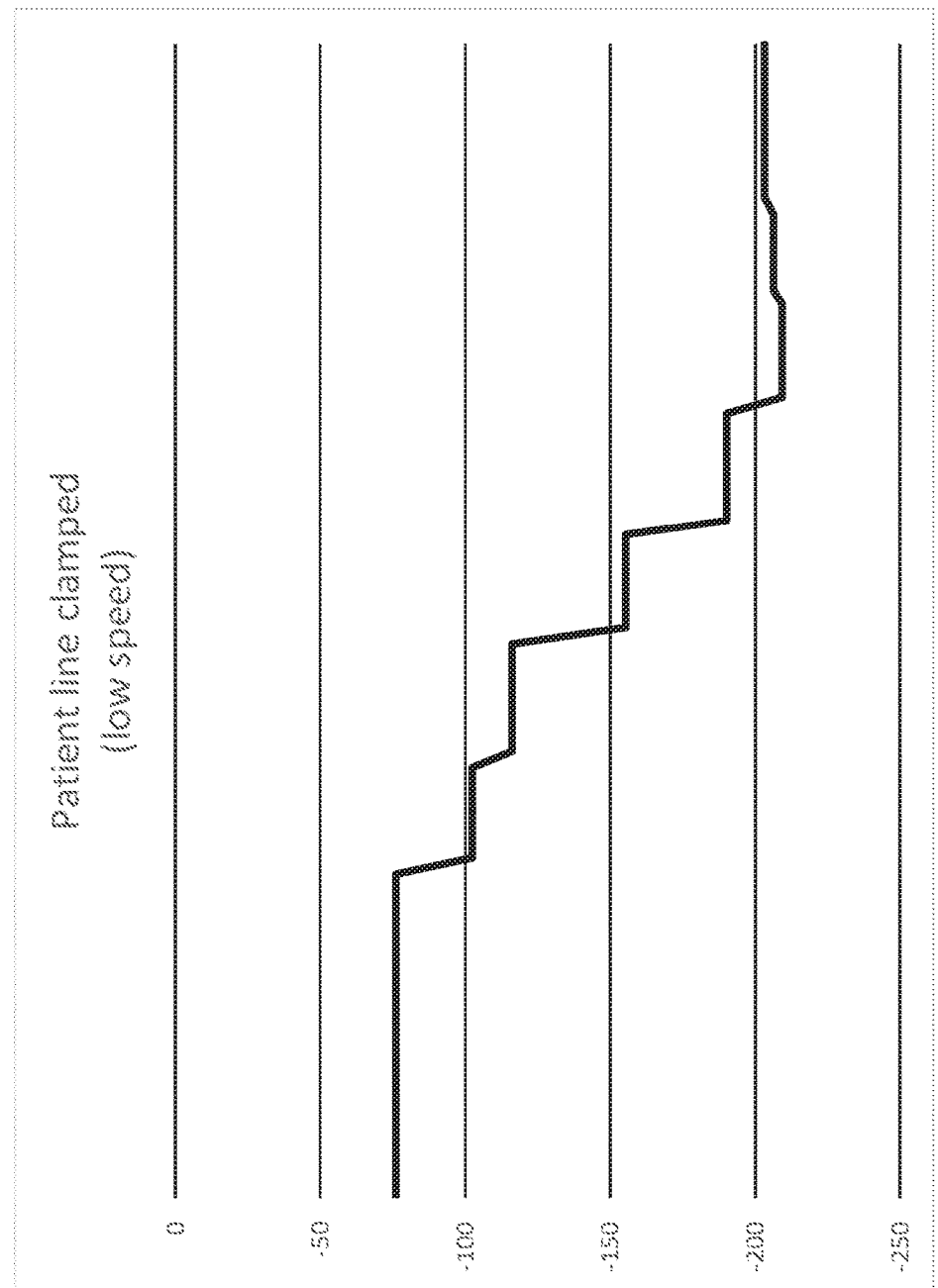

FIGS. 16C and 16D depict the pressure sensor signal generated during normal operation of a drain phase of a PD cycle with the patient line 130 clamped (i.e., fully occluded). The time periods for both charts span approximately 60 seconds. In both cases, the negative pressure differential builds up until the pressure differential reaches a maximum at approximately −200 mbar. It will be appreciated that due to the occlusion, the pressure sensor signal is similar for both the high speed operation and the low speed operation as the pumping mechanism tries and fails to pump effluent dialysate from the patient's abdomen 1006 through the patient line 130. The PD system 100 (e.g., the control unit 139) can detect this negative pressure differential and the low fluid flow condition to infer that there may be an occlusion of the patient line 130.

Figure 16E:
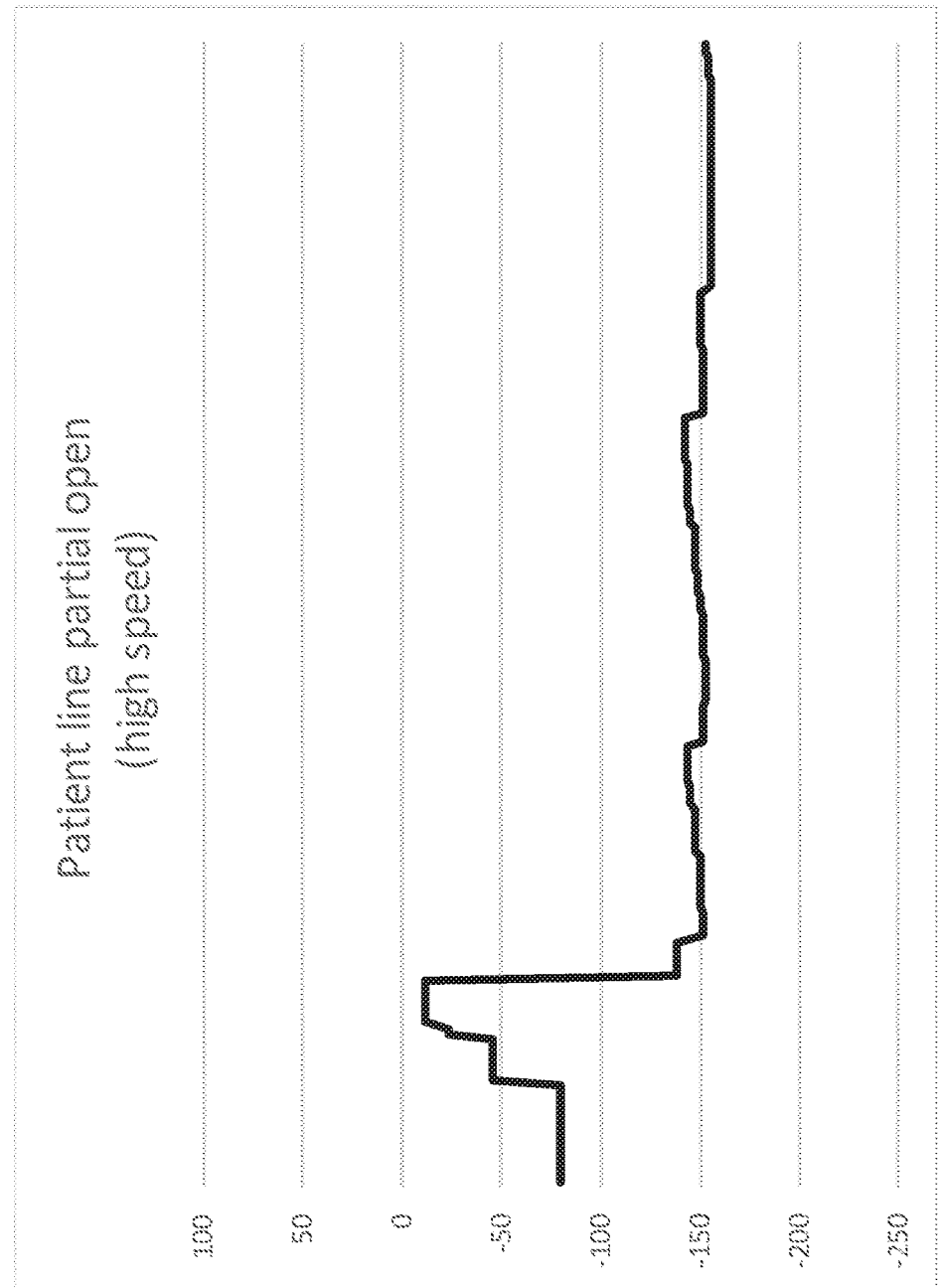
Figure 16F:
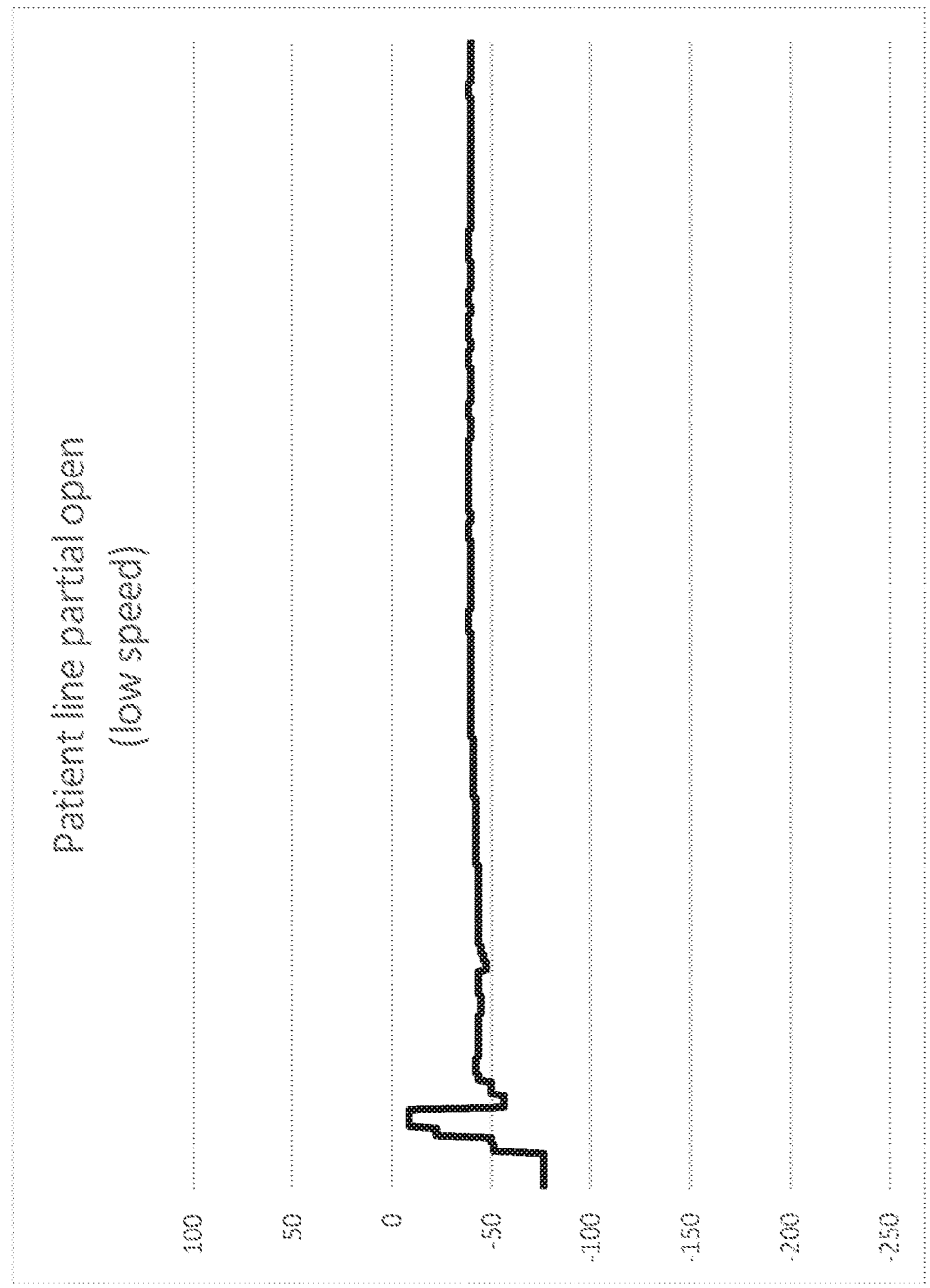

FIGS. 16E and 16F depict the pressure sensor signal generated during normal operation of a drain phase of a PD cycle with the patient line 130 partially open (i.e., partially occluded). The time periods for the high speed operation spans approximately 150 seconds and the time period for the low speed operation spans approximately 500 seconds. In both cases, the negative pressure differential reaches a steady state due to the partial occlusion. However, the pressure differential in the patient line 130 during the low speed operation (e.g., ~−40 mbars) is nearly identical to the pressure differential in the patient line 130 when the patient line is not occluded. In other words, the slower operation permits enough fluid to flow through the restricted patient line in order to fill the pump chambers 138A, 138B with fluid during a full stroke of the pistons 133A, 133B. In contrast, the pressure differential in the patient line 130 during the high speed operation (e.g., ~−150 mbars) is greater than the pressure differential in the patient line 130 when the patient line is not occluded, and this is indicative of too little time for fluid to fill the pump chambers 138A, 138B during each stroke of the pistons 133A, 133B. In other words, the restricted flow cannot keep up with the rate of the pumps. In such cases, there is a failure mode where the negative pressure differential can cause a separation of the piston heads 134A, 134B with the rigid dome-shaped fastening members 161A, 161B. Consequently, a full stroke test (e.g., determining whether fluid volume in the pump chamber after a full stroke of the piston 133A, 133B is greater than a threshold value) during high speed operation could potentially fail whereas the full stroke test during low speed operation may pass due to the increased time for fluid to fill the pump chamber during a slower stroke.

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines involving the transmission of fluid to and from a patient via a patient line and for which patient line checks and occlusion detection would be beneficially performed. For example, the system and techniques described herein may be used in connection with a PD cycler using a different configuration and style of pump, such as a peristaltic pump, and may be used in connection with other types of dialysate heating arrangements, such as in-line heating arrangements.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A peritoneal dialysis (PD) system, comprising:
   at least one pump configured to provide or withdraw fluid from a line connected to a catheter inserted into a peritoneal cavity of a patient;
   a cassette including at least one pump chamber and at least one pressure sensing chamber fluidly coupled to the at least one pump chamber, wherein the line is fluidly coupled to the at least one pump chamber; and
   a processor configured to:
      detect a low fluid flow condition during a phase of a PD cycle,
      responsive to the low fluid flow condition, adjust operating parameters of the at least one pump to reduce a speed of the at least one pump from a first speed to a second speed that is less than the first speed; and
      detect a low fluid volume condition while the at least one pump is operated at the second speed, wherein detecting the low fluid volume condition comprises detecting that a volume of fluid that enters the at least one pump chamber during a retraction stroke of any piston included in the at least one pump during each of a consecutive number of strokes at the second speed is less than a threshold volume of fluid, and wherein the consecutive number of strokes is at least two consecutive retraction strokes.

2. The PD system of claim 1, wherein the processor is configured to, after detecting the low fluid volume condition, perform one or more of:
   trigger an alarm; or
   terminate the phase of the PD cycle.

3. The PD system of claim 1, wherein detecting the low fluid flow condition comprises detecting that a fluid flow rate over a period of time is less than a threshold value.

4. The PD system of claim 3, wherein the threshold value is less than or equal to 30 milliliters per minute and the period of time is at least 5 minutes.

5. The PD system of claim 1, wherein the low fluid flow condition comprises determining that a total volume of fluid drained from the peritoneal cavity during a drain phase of the PD cycle is less than a threshold value after a period of time has elapsed, the period of time measured from the start of the drain phase of the PD cycle.

6. The PD system of claim 5, wherein the threshold value is equal to 35 percent of an expected drain volume and the period of time is 50 percent of an expected drain time.

7. The PD system of claim 5, wherein the threshold value is equal to 70 percent of an expected drain volume and the period of time is an expected drain time.

8. The PD system of claim 1, wherein the consecutive number of strokes is equal to or greater than four consecutive retraction strokes of any piston included in the at least one pump and the threshold volume is less than or equal to 1.5 milliliters.

9. The PD system of claim 1, wherein the processor is further configured to determine that a drain exit criteria is met.

10. The PD system of claim 1, wherein the at least one pump comprises:
   a first piston configured to move towards the cassette to decrease a volume of a first pump chamber of the at least one pump chamber and move away from the cassette to increase the volume of the first pump chamber of the at least one pump chamber; and a second piston configured to move towards the cassette to decrease a volume of a second pump chamber of the at least one pump chamber and move away from the cassette to increase the volume of the second pump chamber of the at least one pump chamber, wherein a first side of the cassette is disposed proximate a cassette interface of a PD machine and a second side of the cassette is disposed proximate a door that applies a force to at least one region of the second side of the cassette to hold the cassette against the cassette interface.

11. The PD system of claim 10, the system further comprising:

a number of inflatable members configured to open a fluid path between the line and the at least one pump chamber.

12. A method of operating a peritoneal dialysis (PD) machine, the method comprising:

operating one or more pumps during a drain phase of a PD cycle to drain effluent dialysate from a peritoneal cavity of a patient fluidly coupled to the PD machine, wherein a distal end of a patient line is attached to a catheter inserted into the peritoneal cavity of the patient and a proximal end of the patient line is attached to a port of a cassette inserted into the PD machine, wherein the cassette includes at least one pump chamber and at least one sensing chamber fluidly coupled to the at least one pump chamber, and wherein the patient line is fluidly connected to the at least one pump chamber;

detecting a low fluid flow condition during the drain phase;

adjusting, responsive to the low fluid flow condition, operating parameters of the one or more pumps to reduce a speed of the at least one pump from a first speed to a second speed that is less than the first speed; and detecting, after adjusting the operating parameters to reduce the speed of the at least one pump from the first speed to the second speed, a low fluid volume condition, wherein detecting the low fluid volume condition comprises detecting that a volume of fluid that enters the at least one pump chamber during a retraction stroke of any piston included in the one or more pumps during each of a consecutive number of strokes at the adjusted operating parameters is less than a threshold volume of fluid, and wherein the consecutive number of strokes is at least two consecutive retraction strokes.

13. The method of claim 12, further comprising, after detecting the low fluid volume condition, performing one or more of:

triggering an alarm; or terminating the drain phase of the PD cycle.

14. The method of claim 12, wherein the low fluid flow condition comprises detecting that a fluid flow rate over a period of time is less than a threshold value.

15. The method of claim 12, wherein the low fluid flow condition comprises determining that a total volume of fluid drained from the peritoneal cavity during the drain phase of the PD cycle is less than a threshold value after a period of time has elapsed, the period of time measured from the start of the drain phase of the PD cycle.

16. The method of claim 12, wherein the consecutive number of strokes is equal to or greater than four retraction strokes of the one or more pumps.

17. The method of claim 12, further comprising, prior to terminating the drain phase of the PD cycle, determining that a drain exit criteria is met.

* * * * *